(12) United States Patent
Todeschini

(10) Patent No.: US 10,373,143 B2
(45) Date of Patent: Aug. 6, 2019

(54) PRODUCT IDENTIFICATION USING ELECTROENCEPHALOGRAPHY

(71) Applicant: Hand Held Products, Inc., Fort Mill, SC (US)

(72) Inventor: Erik Todeschini, Camillus, NY (US)

(73) Assignee: Hand Held Products, Inc., Fort Mill, SC (US)

( * ) Notice: Subject to any disclaimer, the term of this patent is extended or adjusted under 35 U.S.C. 154(b) by 691 days.

(21) Appl. No.: 14/863,681

(22) Filed: Sep. 24, 2015

(65) Prior Publication Data

US 2017/0091741 A1 Mar. 30, 2017

(51) Int. Cl.
| | |
|---|---|
| *G06Q 20/00* | (2012.01) |
| *G06Q 20/20* | (2012.01) |
| *A61B 5/00* | (2006.01) |
| *A61B 5/0476* | (2006.01) |
| *A61B 5/16* | (2006.01) |
| *G07G 1/00* | (2006.01) |

(52) U.S. Cl.
CPC ......... *G06Q 20/201* (2013.01); *A61B 5/0476* (2013.01); *A61B 5/16* (2013.01); *A61B 5/7264* (2013.01); *G06Q 20/208* (2013.01); *G07G 1/0036* (2013.01)

(58) Field of Classification Search
CPC ........................... G06Q 20/201; G06Q 10/087
USPC ........................................................ 705/20
See application file for complete search history.

(56) References Cited

U.S. PATENT DOCUMENTS

| | | | |
|---|---|---|---|
| 6,832,725 B2 | 12/2004 | Gardiner et al. |
| 7,128,266 B2 | 10/2006 | Zhu et al. |
| 7,159,783 B2 | 1/2007 | Walczyk et al. |
| 7,413,127 B2 | 8/2008 | Ehrhart et al. |
| 7,726,575 B2 | 6/2010 | Wang et al. |
| 8,294,969 B2 | 10/2012 | Plesko |
| 8,317,105 B2 | 11/2012 | Kotlarsky et al. |
| 8,322,622 B2 | 12/2012 | Liu et al. |
| 8,366,005 B2 | 2/2013 | Kotlarsky et al. |

(Continued)

FOREIGN PATENT DOCUMENTS

| | | |
|---|---|---|
| WO | 2013163789 A1 | 11/2013 |
| WO | 2013173985 A1 | 11/2013 |

(Continued)

OTHER PUBLICATIONS

Combined Search and Examination Report in counterpart GB Application No. 1615457.7 dated Feb. 21, 2017, pp. 1-7.

(Continued)

*Primary Examiner* — Rokib Masud
(74) *Attorney, Agent, or Firm* — Additon, Higgins & Pendleton, P.A.

(57) ABSTRACT

An EEG POS system has an EEG device that detects electrical signals representing brain waves. A database of brain wave profiles represents a plurality of items to be identified. A live signal analyzer compares electrical signals from the EEG device with stored brain wave profiles in the database to identify entries in the database representing items that match the electrical signals from the EEG device, where items whose stored brain wave profiles match the electrical signals are considered identified items. A POS terminal is coupled to the live signal analyzer in order to log and tally items for a transaction.

13 Claims, 4 Drawing Sheets

(56) References Cited

U.S. PATENT DOCUMENTS

| | | | |
|---|---|---|---|
| 8,371,507 B2 | 2/2013 | Haggerty et al. |
| 8,376,233 B2 | 2/2013 | Van Horn et al. |
| 8,381,979 B2 | 2/2013 | Franz |
| 8,390,909 B2 | 3/2013 | Plesko |
| 8,408,464 B2 | 4/2013 | Zhu et al. |
| 8,408,468 B2 | 4/2013 | Horn et al. |
| 8,408,469 B2 | 4/2013 | Good |
| 8,424,768 B2 | 4/2013 | Rueblinger et al. |
| 8,448,863 B2 | 5/2013 | Xian et al. |
| 8,457,013 B2 | 6/2013 | Essinger et al. |
| 8,459,557 B2 | 6/2013 | Havens et al. |
| 8,469,272 B2 | 6/2013 | Kearney |
| 8,474,712 B2 | 7/2013 | Kearney et al. |
| 8,479,992 B2 | 7/2013 | Kotlarsky et al. |
| 8,490,877 B2 | 7/2013 | Kearney |
| 8,517,271 B2 | 8/2013 | Kotlarsky et al. |
| 8,523,076 B2 | 9/2013 | Good |
| 8,528,818 B2 | 9/2013 | Ehrhart et al. |
| 8,544,737 B2 | 10/2013 | Gomez et al. |
| 8,548,420 B2 | 10/2013 | Grunow et al. |
| 8,550,335 B2 | 10/2013 | Samek et al. |
| 8,550,354 B2 | 10/2013 | Gannon et al. |
| 8,550,357 B2 | 10/2013 | Kearney |
| 8,556,174 B2 | 10/2013 | Kosecki et al. |
| 8,556,176 B2 | 10/2013 | Van Horn et al. |
| 8,556,177 B2 | 10/2013 | Hussey et al. |
| 8,559,767 B2 | 10/2013 | Barber et al. |
| 8,561,895 B2 | 10/2013 | Gomez et al. |
| 8,561,903 B2 | 10/2013 | Sauerwein |
| 8,561,905 B2 | 10/2013 | Edmonds et al. |
| 8,565,107 B2 | 10/2013 | Pease et al. |
| 8,571,307 B2 | 10/2013 | Li et al. |
| 8,579,200 B2 | 11/2013 | Samek et al. |
| 8,583,924 B2 | 11/2013 | Caballero et al. |
| 8,584,945 B2 | 11/2013 | Wang et al. |
| 8,587,595 B2 | 11/2013 | Wang |
| 8,587,697 B2 | 11/2013 | Hussey et al. |
| 8,588,869 B2 | 11/2013 | Sauerwein et al. |
| 8,590,789 B2 | 11/2013 | Nahill et al. |
| 8,596,539 B2 | 12/2013 | Havens et al. |
| 8,596,542 B2 | 12/2013 | Havens et al. |
| 8,596,543 B2 | 12/2013 | Havens et al. |
| 8,599,271 B2 | 12/2013 | Havens et al. |
| 8,599,957 B2 | 12/2013 | Peake et al. |
| 8,600,158 B2 | 12/2013 | Li et al. |
| 8,600,167 B2 | 12/2013 | Showering |
| 8,602,309 B2 | 12/2013 | Longacre et al. |
| 8,608,053 B2 | 12/2013 | Meier et al. |
| 8,608,071 B2 | 12/2013 | Liu et al. |
| 8,611,309 B2 | 12/2013 | Wang et al. |
| 8,615,487 B2 | 12/2013 | Gomez et al. |
| 8,621,123 B2 | 12/2013 | Caballero |
| 8,622,303 B2 | 1/2014 | Meier et al. |
| 8,628,013 B2 | 1/2014 | Ding |
| 8,628,015 B2 | 1/2014 | Wang et al. |
| 8,628,016 B2 | 1/2014 | Winegar |
| 8,629,926 B2 | 1/2014 | Wang |
| 8,630,491 B2 | 1/2014 | Longacre et al. |
| 8,635,309 B2 | 1/2014 | Berthiaume et al. |
| 8,636,200 B2 | 1/2014 | Kearney |
| 8,636,212 B2 | 1/2014 | Nahill et al. |
| 8,636,215 B2 | 1/2014 | Ding et al. |
| 8,636,224 B2 | 1/2014 | Wang |
| 8,638,806 B2 | 1/2014 | Wang et al. |
| 8,640,958 B2 | 2/2014 | Lu et al. |
| 8,640,960 B2 | 2/2014 | Wang et al. |
| 8,643,717 B2 | 2/2014 | Li et al. |
| 8,646,692 B2 | 2/2014 | Meier et al. |
| 8,646,694 B2 | 2/2014 | Wang et al. |
| 8,657,200 B2 | 2/2014 | Ren et al. |
| 8,659,397 B2 | 2/2014 | Vargo et al. |
| 8,668,149 B2 | 3/2014 | Good |
| 8,678,285 B2 | 3/2014 | Kearney |
| 8,678,286 B2 | 3/2014 | Smith et al. |
| 8,682,077 B1 | 3/2014 | Longacre |
| D702,237 S | 4/2014 | Oberpriller et al. |
| 8,687,282 B2 | 4/2014 | Feng et al. |
| 8,692,927 B2 | 4/2014 | Pease et al. |
| 8,695,880 B2 | 4/2014 | Bremer et al. |
| 8,698,949 B2 | 4/2014 | Grunow et al. |
| 8,702,000 B2 | 4/2014 | Barber et al. |
| 8,717,494 B2 | 5/2014 | Gannon |
| 8,720,783 B2 | 5/2014 | Biss et al. |
| 8,723,804 B2 | 5/2014 | Fletcher et al. |
| 8,723,904 B2 | 5/2014 | Marty et al. |
| 8,727,223 B2 | 5/2014 | Wang |
| 8,740,082 B2 | 6/2014 | Wilz |
| 8,740,085 B2 | 6/2014 | Furlong et al. |
| 8,746,563 B2 | 6/2014 | Hennick et al. |
| 8,750,445 B2 | 6/2014 | Peake et al. |
| 8,752,766 B2 | 6/2014 | Xian et al. |
| 8,756,059 B2 | 6/2014 | Braho et al. |
| 8,757,495 B2 | 6/2014 | Qu et al. |
| 8,760,563 B2 | 6/2014 | Koziol et al. |
| 8,763,909 B2 | 7/2014 | Reed et al. |
| 8,777,108 B2 | 7/2014 | Coyle |
| 8,777,109 B2 | 7/2014 | Oberpriller et al. |
| 8,779,898 B2 | 7/2014 | Havens et al. |
| 8,781,520 B2 | 7/2014 | Payne et al. |
| 8,783,573 B2 | 7/2014 | Havens et al. |
| 8,789,757 B2 | 7/2014 | Barten |
| 8,789,758 B2 | 7/2014 | Hawley et al. |
| 8,789,759 B2 | 7/2014 | Xian et al. |
| 8,794,520 B2 | 8/2014 | Wang et al. |
| 8,794,522 B2 | 8/2014 | Ehrhart |
| 8,794,525 B2 | 8/2014 | Amundsen et al. |
| 8,794,526 B2 | 8/2014 | Wang et al. |
| 8,798,367 B2 | 8/2014 | Ellis |
| 8,807,431 B2 | 8/2014 | Wang et al. |
| 8,807,432 B2 | 8/2014 | Van Horn et al. |
| 8,820,630 B2 | 9/2014 | Qu et al. |
| 8,822,848 B2 | 9/2014 | Meagher |
| 8,824,692 B2 | 9/2014 | Sheerin et al. |
| 8,824,696 B2 | 9/2014 | Braho |
| 8,842,849 B2 | 9/2014 | Wahl et al. |
| 8,844,822 B2 | 9/2014 | Kotlarsky et al. |
| 8,844,823 B2 | 9/2014 | Fritz et al. |
| 8,849,019 B2 | 9/2014 | Li et al. |
| D716,285 S | 10/2014 | Chaney et al. |
| 8,851,383 B2 | 10/2014 | Yeakley et al. |
| 8,854,633 B2 | 10/2014 | Laffargue |
| 8,866,963 B2 | 10/2014 | Grunow et al. |
| 8,868,421 B2 | 10/2014 | Braho et al. |
| 8,868,519 B2 | 10/2014 | Maloy et al. |
| 8,868,802 B2 | 10/2014 | Barten |
| 8,868,803 B2 | 10/2014 | Caballero |
| 8,870,074 B1 | 10/2014 | Gannon |
| 8,879,639 B2 | 11/2014 | Sauerwein |
| 8,880,426 B2 | 11/2014 | Smith |
| 8,881,983 B2 | 11/2014 | Havens et al. |
| 8,881,987 B2 | 11/2014 | Wang |
| 8,903,172 B2 | 12/2014 | Smith |
| 8,908,995 B2 | 12/2014 | Benos et al. |
| 8,910,870 B2 | 12/2014 | Li et al. |
| 8,910,875 B2 | 12/2014 | Ren et al. |
| 8,914,290 B2 | 12/2014 | Hendrickson et al. |
| 8,914,788 B2 | 12/2014 | Pettinelli et al. |
| 8,915,439 B2 | 12/2014 | Feng et al. |
| 8,915,444 B2 | 12/2014 | Havens et al. |
| 8,916,789 B2 | 12/2014 | Woodburn |
| 8,918,250 B2 | 12/2014 | Hollifield |
| 8,918,564 B2 | 12/2014 | Caballero |
| 8,925,818 B2 | 1/2015 | Kosecki et al. |
| 8,939,374 B2 | 1/2015 | Jovanovski et al. |
| 8,942,480 B2 | 1/2015 | Ellis |
| 8,944,313 B2 | 2/2015 | Williams et al. |
| 8,944,327 B2 | 2/2015 | Meier et al. |
| 8,944,332 B2 | 2/2015 | Harding et al. |
| 8,950,678 B2 | 2/2015 | Germaine et al. |
| D723,560 S | 3/2015 | Zhou et al. |
| 8,967,468 B2 | 3/2015 | Gomez et al. |
| 8,971,346 B2 | 3/2015 | Sevier |
| 8,976,030 B2 | 3/2015 | Cunningham et al. |
| 8,976,368 B2 | 3/2015 | Akel et al. |

(56) References Cited

U.S. PATENT DOCUMENTS

| | | |
|---|---|---|
| 8,978,981 B2 | 3/2015 | Guan |
| 8,978,983 B2 | 3/2015 | Bremer et al. |
| 8,978,984 B2 | 3/2015 | Hennick et al. |
| 8,985,456 B2 | 3/2015 | Zhu et al. |
| 8,985,457 B2 | 3/2015 | Soule et al. |
| 8,985,459 B2 | 3/2015 | Kearney et al. |
| 8,985,461 B2 | 3/2015 | Gelay et al. |
| 8,988,578 B2 | 3/2015 | Showering |
| 8,988,590 B2 | 3/2015 | Gillet et al. |
| 8,991,704 B2 | 3/2015 | Hopper et al. |
| 8,996,194 B2 | 3/2015 | Davis et al. |
| 8,996,384 B2 | 3/2015 | Funyak et al. |
| 8,998,091 B2 | 4/2015 | Edmonds et al. |
| 9,002,641 B2 | 4/2015 | Showering |
| 9,007,368 B2 | 4/2015 | Laffargue et al. |
| 9,010,641 B2 | 4/2015 | Qu et al. |
| 9,015,513 B2 | 4/2015 | Murawski et al. |
| 9,016,576 B2 | 4/2015 | Brady et al. |
| D730,357 S | 5/2015 | Fitch et al. |
| 9,022,288 B2 | 5/2015 | Nahill et al. |
| 9,030,964 B2 | 5/2015 | Essinger et al. |
| 9,033,240 B2 | 5/2015 | Smith et al. |
| 9,033,242 B2 | 5/2015 | Gillet et al. |
| 9,036,054 B2 | 5/2015 | Koziol et al. |
| 9,037,344 B2 | 5/2015 | Chamberlin |
| 9,038,911 B2 | 5/2015 | Xian et al. |
| 9,038,915 B2 | 5/2015 | Smith |
| D730,901 S | 6/2015 | Oberpriller et al. |
| D730,902 S | 6/2015 | Fitch et al. |
| D733,112 S | 6/2015 | Chaney et al. |
| 9,047,098 B2 | 6/2015 | Barten |
| 9,047,359 B2 | 6/2015 | Caballero et al. |
| 9,047,420 B2 | 6/2015 | Caballero |
| 9,047,525 B2 | 6/2015 | Barber |
| 9,047,531 B2 | 6/2015 | Showering et al. |
| 9,049,640 B2 | 6/2015 | Wang et al. |
| 9,053,055 B2 | 6/2015 | Caballero |
| 9,053,378 B1 | 6/2015 | Hou et al. |
| 9,053,380 B2 | 6/2015 | Xian et al. |
| 9,057,641 B2 | 6/2015 | Amundsen et al. |
| 9,058,526 B2 | 6/2015 | Powilleit |
| 9,064,165 B2 | 6/2015 | Havens et al. |
| 9,064,167 B2 | 6/2015 | Xian et al. |
| 9,064,168 B2 | 6/2015 | Todeschini et al. |
| 9,064,254 B2 | 6/2015 | Todeschini et al. |
| 9,066,032 B2 | 6/2015 | Wang |
| 9,070,032 B2 | 6/2015 | Corcoran |
| D734,339 S | 7/2015 | Zhou et al. |
| D734,751 S | 7/2015 | Oberpriller et al. |
| 9,082,023 B2 | 7/2015 | Feng et al. |
| 9,224,022 B2 | 12/2015 | Ackley et al. |
| 9,224,027 B2 | 12/2015 | Van Horn et al. |
| D747,321 S | 1/2016 | London et al. |
| 9,230,140 B1 | 1/2016 | Ackley |
| 9,443,123 B2 | 1/2016 | Hejl |
| 9,250,712 B1 | 2/2016 | Todeschini |
| 9,258,033 B2 | 2/2016 | Showering |
| 9,262,633 B1 | 2/2016 | Todeschini et al. |
| 9,310,609 B2 | 4/2016 | Rueblinger et al. |
| D757,009 S | 5/2016 | Oberpriller et al. |
| 9,342,724 B2 | 5/2016 | McCloskey |
| 9,375,945 B1 | 6/2016 | Bowles |
| D760,719 S | 7/2016 | Zhou et al. |
| 9,390,596 B1 | 7/2016 | Todeschini |
| D762,604 S | 8/2016 | Fitch et al. |
| D762,647 S | 8/2016 | Fitch et al. |
| 9,412,242 B2 | 8/2016 | Van Horn et al. |
| D766,244 S | 9/2016 | Zhou et al. |
| 9,443,222 B2 | 9/2016 | Singel et al. |
| 9,478,113 B2 | 10/2016 | Xie et al. |
| 9,507,974 B1 | 11/2016 | Todeschini |
| 2006/0258408 A1 | 11/2006 | Tuomela et al. |
| 2007/0010756 A1 | 1/2007 | Viertio-Oja |
| 2007/0063048 A1 | 3/2007 | Havens et al. |
| 2007/0123350 A1* | 5/2007 | Soderlund ............ A61B 5/0476 463/36 |
| 2007/0124027 A1 | 5/2007 | Betziza et al. |
| 2007/0168461 A1* | 7/2007 | Moore ................. G06F 19/328 709/217 |
| 2008/0228365 A1 | 9/2008 | White et al. |
| 2009/0040054 A1 | 2/2009 | Wang et al. |
| 2009/0134221 A1 | 5/2009 | Zhu et al. |
| 2009/0227965 A1 | 9/2009 | Wijesiriwardana |
| 2010/0094502 A1 | 4/2010 | Ito |
| 2010/0145218 A1 | 6/2010 | Adachi et al. |
| 2010/0177076 A1 | 7/2010 | Essinger et al. |
| 2010/0177080 A1 | 7/2010 | Essinger et al. |
| 2010/0177707 A1 | 7/2010 | Essinger et al. |
| 2010/0177749 A1 | 7/2010 | Essinger et al. |
| 2010/0324936 A1* | 12/2010 | Vishnubhatla ........ G06F 19/328 705/3 |
| 2011/0169999 A1 | 7/2011 | Grunow et al. |
| 2011/0187640 A1 | 8/2011 | Jacobsen et al. |
| 2011/0202554 A1 | 8/2011 | Powilleit et al. |
| 2011/0213511 A1 | 9/2011 | Visconti et al. |
| 2011/0247027 A1* | 10/2011 | Davis ................ H04N 21/25435 725/5 |
| 2012/0046531 A1 | 2/2012 | Hua |
| 2012/0108995 A1 | 5/2012 | Pradeep et al. |
| 2012/0111946 A1 | 5/2012 | Golant |
| 2012/0168512 A1 | 7/2012 | Kotlarsky et al. |
| 2012/0172744 A1* | 7/2012 | Kato ..................... A61B 5/0478 600/544 |
| 2012/0193423 A1 | 8/2012 | Samek |
| 2012/0203647 A1 | 8/2012 | Smith |
| 2012/0223141 A1 | 9/2012 | Good et al. |
| 2013/0043312 A1 | 2/2013 | Van Horn |
| 2013/0075168 A1 | 3/2013 | Amundsen et al. |
| 2013/0130799 A1 | 5/2013 | Van Hulle et al. |
| 2013/0175341 A1 | 7/2013 | Kearney et al. |
| 2013/0175343 A1 | 7/2013 | Good |
| 2013/0204153 A1 | 8/2013 | Buzhardt |
| 2013/0226408 A1 | 8/2013 | Fung et al. |
| 2013/0239187 A1* | 9/2013 | Leddy .................. H04L 9/3226 726/6 |
| 2013/0257744 A1 | 10/2013 | Daghigh et al. |
| 2013/0257759 A1 | 10/2013 | Daghigh |
| 2013/0270346 A1 | 10/2013 | Xian et al. |
| 2013/0287258 A1 | 10/2013 | Kearney |
| 2013/0292475 A1 | 11/2013 | Kotlarsky et al. |
| 2013/0292477 A1 | 11/2013 | Hennick et al. |
| 2013/0293539 A1 | 11/2013 | Hunt et al. |
| 2013/0293540 A1 | 11/2013 | Laffargue et al. |
| 2013/0296731 A1 | 11/2013 | Kidmose et al. |
| 2013/0306728 A1 | 11/2013 | Thuries et al. |
| 2013/0306731 A1 | 11/2013 | Pedraro |
| 2013/0307964 A1 | 11/2013 | Bremer et al. |
| 2013/0308625 A1 | 11/2013 | Park et al. |
| 2013/0313324 A1 | 11/2013 | Koziol et al. |
| 2013/0313325 A1 | 11/2013 | Wilz et al. |
| 2013/0342717 A1 | 12/2013 | Havens et al. |
| 2014/0001267 A1 | 1/2014 | Giordano et al. |
| 2014/0002828 A1 | 1/2014 | Laffargue et al. |
| 2014/0008439 A1 | 1/2014 | Wang |
| 2014/0025584 A1 | 1/2014 | Liu et al. |
| 2014/0100813 A1 | 1/2014 | Showering |
| 2014/0034734 A1 | 2/2014 | Sauerwein |
| 2014/0036848 A1 | 2/2014 | Pease et al. |
| 2014/0039693 A1 | 2/2014 | Havens et al. |
| 2014/0042814 A1 | 2/2014 | Kather et al. |
| 2014/0049120 A1 | 2/2014 | Kohtz et al. |
| 2014/0049635 A1 | 2/2014 | Laffargue et al. |
| 2014/0061306 A1 | 3/2014 | Wu et al. |
| 2014/0063289 A1 | 3/2014 | Hussey et al. |
| 2014/0066136 A1 | 3/2014 | Sauerwein et al. |
| 2014/0067692 A1 | 3/2014 | Ye et al. |
| 2014/0070005 A1 | 3/2014 | Nahill et al. |
| 2014/0071840 A1 | 3/2014 | Venancio |
| 2014/0074746 A1 | 3/2014 | Wang |
| 2014/0076974 A1 | 3/2014 | Havens et al. |
| 2014/0078341 A1 | 3/2014 | Havens et al. |
| 2014/0078342 A1 | 3/2014 | Li et al. |
| 2014/0078345 A1 | 3/2014 | Showering |

(56) References Cited

U.S. PATENT DOCUMENTS

| | | |
|---|---|---|
| 2014/0098792 A1 | 4/2014 | Wang et al. |
| 2014/0100774 A1 | 4/2014 | Showering |
| 2014/0103115 A1 | 4/2014 | Meier et al. |
| 2014/0104413 A1 | 4/2014 | McCloskey et al. |
| 2014/0104414 A1 | 4/2014 | McCloskey et al. |
| 2014/0104416 A1 | 4/2014 | Giordano et al. |
| 2014/0104451 A1 | 4/2014 | Todeschini et al. |
| 2014/0106594 A1 | 4/2014 | Skvoretz |
| 2014/0106725 A1 | 4/2014 | Sauerwein |
| 2014/0108010 A1 | 4/2014 | Maltseff et al. |
| 2014/0108402 A1 | 4/2014 | Gomez et al. |
| 2014/0108682 A1 | 4/2014 | Caballero |
| 2014/0110485 A1 | 4/2014 | Toa et al. |
| 2014/0114530 A1 | 4/2014 | Fitch et al. |
| 2014/0124577 A1 | 5/2014 | Wang et al. |
| 2014/0124579 A1 | 5/2014 | Ding |
| 2014/0125842 A1 | 5/2014 | Winegar |
| 2014/0125853 A1 | 5/2014 | Wang |
| 2014/0125999 A1 | 5/2014 | Longacre et al. |
| 2014/0129378 A1 | 5/2014 | Richardson |
| 2014/0131438 A1 | 5/2014 | Kearney |
| 2014/0131441 A1 | 5/2014 | Nahill et al. |
| 2014/0131443 A1 | 5/2014 | Smith |
| 2014/0131444 A1 | 5/2014 | Wang |
| 2014/0131445 A1 | 5/2014 | Ding et al. |
| 2014/0131448 A1 | 5/2014 | Xian et al. |
| 2014/0133379 A1 | 5/2014 | Wang et al. |
| 2014/0136208 A1 | 5/2014 | Maltseff et al. |
| 2014/0140585 A1 | 5/2014 | Wang |
| 2014/0151453 A1 | 6/2014 | Meier et al. |
| 2014/0152882 A1 | 6/2014 | Samek et al. |
| 2014/0158770 A1 | 6/2014 | Sevier et al. |
| 2014/0159869 A1 | 6/2014 | Zumsteg et al. |
| 2014/0166755 A1 | 6/2014 | Liu et al. |
| 2014/0166757 A1 | 6/2014 | Smith |
| 2014/0166759 A1 | 6/2014 | Liu et al. |
| 2014/0168787 A1 | 6/2014 | Wang et al. |
| 2014/0175165 A1 | 6/2014 | Havens et al. |
| 2014/0175172 A1 | 6/2014 | Jovanovski et al. |
| 2014/0191644 A1 | 7/2014 | Chaney |
| 2014/0191913 A1 | 7/2014 | Ge et al. |
| 2014/0197238 A1 | 7/2014 | Lui et al. |
| 2014/0197239 A1 | 7/2014 | Havens et al. |
| 2014/0197304 A1 | 7/2014 | Feng et al. |
| 2014/0203087 A1 | 7/2014 | Smith et al. |
| 2014/0204268 A1 | 7/2014 | Grunow et al. |
| 2014/0206323 A1 | 7/2014 | Scorcioni |
| 2014/0214631 A1 | 7/2014 | Hansen |
| 2014/0217166 A1 | 8/2014 | Berthiaume et al. |
| 2014/0217180 A1 | 8/2014 | Liu |
| 2014/0231500 A1 | 8/2014 | Ehrhart et al. |
| 2014/0232930 A1 | 8/2014 | Anderson |
| 2014/0247315 A1 | 9/2014 | Marty et al. |
| 2014/0263493 A1 | 9/2014 | Amurgis et al. |
| 2014/0263645 A1 | 9/2014 | Smith et al. |
| 2014/0270196 A1 | 9/2014 | Braho et al. |
| 2014/0270229 A1 | 9/2014 | Braho |
| 2014/0278387 A1 | 9/2014 | DiGregorio |
| 2014/0282210 A1 | 9/2014 | Bianconi |
| 2014/0284384 A1 | 9/2014 | Lu et al. |
| 2014/0285404 A1 | 9/2014 | Takano et al. |
| 2014/0288933 A1 | 9/2014 | Braho et al. |
| 2014/0297058 A1 | 10/2014 | Barker et al. |
| 2014/0299665 A1 | 10/2014 | Barber et al. |
| 2014/0312121 A1 | 10/2014 | Lu et al. |
| 2014/0319220 A1 | 10/2014 | Coyle |
| 2014/0319221 A1 | 10/2014 | Oberpriller et al. |
| 2014/0326787 A1 | 11/2014 | Barten |
| 2014/0332590 A1 | 11/2014 | Wang et al. |
| 2014/0334083 A1 | 11/2014 | Bailey |
| 2014/0344943 A1 | 11/2014 | Todeschini et al. |
| 2014/0346233 A1 | 11/2014 | Liu et al. |
| 2014/0351317 A1 | 11/2014 | Smith et al. |
| 2014/0353373 A1 | 12/2014 | Van Horn et al. |
| 2014/0361073 A1 | 12/2014 | Qu et al. |
| 2014/0361082 A1 | 12/2014 | Xian et al. |
| 2014/0362184 A1 | 12/2014 | Jovanovski et al. |
| 2014/0363015 A1 | 12/2014 | Braho |
| 2014/0369511 A1 | 12/2014 | Sheerin et al. |
| 2014/0374483 A1 | 12/2014 | Lu |
| 2014/0374485 A1 | 12/2014 | Xian et al. |
| 2015/0001301 A1 | 1/2015 | Ouyang |
| 2015/0001304 A1 | 1/2015 | Todeschini |
| 2015/0003673 A1 | 1/2015 | Fletcher |
| 2015/0009338 A1 | 1/2015 | Laffargue et al. |
| 2015/0009610 A1 | 1/2015 | London et al. |
| 2015/0012426 A1* | 1/2015 | Purves ............... G06Q 30/0623 705/41 |
| 2015/0014416 A1 | 1/2015 | Kotlarsky et al. |
| 2015/0021397 A1 | 1/2015 | Rueblinger et al. |
| 2015/0028102 A1 | 1/2015 | Ren et al. |
| 2015/0028103 A1 | 1/2015 | Jiang |
| 2015/0028104 A1 | 1/2015 | Ma et al. |
| 2015/0029002 A1 | 1/2015 | Yeakley et al. |
| 2015/0032709 A1 | 1/2015 | Maloy et al. |
| 2015/0039309 A1 | 2/2015 | Braho et al. |
| 2015/0040378 A1 | 2/2015 | Saber et al. |
| 2015/0048168 A1 | 2/2015 | Fritz et al. |
| 2015/0049347 A1 | 2/2015 | Laffargue et al. |
| 2015/0051992 A1 | 2/2015 | Smith |
| 2015/0053766 A1 | 2/2015 | Havens et al. |
| 2015/0053768 A1 | 2/2015 | Wang et al. |
| 2015/0053769 A1 | 2/2015 | Thuries et al. |
| 2015/0062366 A1 | 3/2015 | Liu et al. |
| 2015/0063215 A1 | 3/2015 | Wang |
| 2015/0063676 A1 | 3/2015 | Lloyd et al. |
| 2015/0069130 A1 | 3/2015 | Gannon |
| 2015/0071819 A1 | 3/2015 | Todeschini |
| 2015/0073907 A1* | 3/2015 | Purves ............... G06Q 20/32 705/14.58 |
| 2015/0083800 A1 | 3/2015 | Li et al. |
| 2015/0086114 A1 | 3/2015 | Todeschini |
| 2015/0088522 A1 | 3/2015 | Hendrickson et al. |
| 2015/0096872 A1 | 4/2015 | Woodburn |
| 2015/0099557 A1 | 4/2015 | Pettinelli et al. |
| 2015/0100196 A1 | 4/2015 | Hollifield |
| 2015/0102109 A1 | 4/2015 | Huck |
| 2015/0115035 A1 | 4/2015 | Meier et al. |
| 2015/0127791 A1 | 5/2015 | Kosecki et al. |
| 2015/0128116 A1 | 5/2015 | Chen et al. |
| 2015/0129659 A1 | 5/2015 | Feng et al. |
| 2015/0133047 A1 | 5/2015 | Smith et al. |
| 2015/0134470 A1 | 5/2015 | Hejl et al. |
| 2015/0136851 A1 | 5/2015 | Harding et al. |
| 2015/0136854 A1 | 5/2015 | Lu et al. |
| 2015/0141529 A1 | 5/2015 | Hargrove |
| 2015/0142492 A1 | 5/2015 | Kumar |
| 2015/0144692 A1 | 5/2015 | Hejl |
| 2015/0144698 A1 | 5/2015 | Teng et al. |
| 2015/0144701 A1 | 5/2015 | Xian et al. |
| 2015/0149946 A1 | 5/2015 | Benos et al. |
| 2015/0161429 A1 | 6/2015 | Xian |
| 2015/0169925 A1 | 6/2015 | Chang et al. |
| 2015/0169929 A1 | 6/2015 | Williams et al. |
| 2015/0186703 A1 | 7/2015 | Chen et al. |
| 2015/0193644 A1 | 7/2015 | Kearney et al. |
| 2015/0193645 A1 | 7/2015 | Colavito et al. |
| 2015/0199957 A1 | 7/2015 | Funyak et al. |
| 2015/0204671 A1 | 7/2015 | Showering |
| 2015/0210199 A1 | 7/2015 | Payne |
| 2015/0220753 A1 | 8/2015 | Zhu et al. |
| 2015/0248651 A1* | 9/2015 | Akutagawa ........ G06Q 10/1095 705/7.19 |
| 2015/0254485 A1 | 9/2015 | Feng et al. |
| 2015/0257673 A1 | 9/2015 | Lawrence et al. |
| 2015/0272465 A1 | 10/2015 | Ishii |
| 2015/0282760 A1 | 10/2015 | Badower et al. |
| 2015/0313496 A1 | 11/2015 | Connor |
| 2015/0313497 A1 | 11/2015 | Chang et al. |
| 2015/0313539 A1 | 11/2015 | Connor |
| 2015/0327012 A1 | 11/2015 | Bian et al. |
| 2015/0374255 A1 | 12/2015 | Vasapollo |
| 2016/0004820 A1* | 1/2016 | Moore ................... H04W 4/21 705/3 |

(56) References Cited

U.S. PATENT DOCUMENTS

| | | |
|---|---|---|
| 2016/0014251 A1 | 1/2016 | Hejl |
| 2016/0040982 A1 | 2/2016 | Li et al. |
| 2016/0042241 A1 | 2/2016 | Todeschini |
| 2016/0057230 A1 | 2/2016 | Todeschini et al. |
| 2016/0103487 A1 | 4/2016 | Crawford et al. |
| 2016/0109219 A1 | 4/2016 | Ackley et al. |
| 2016/0109220 A1 | 4/2016 | Laffargue |
| 2016/0109224 A1 | 4/2016 | Thuries et al. |
| 2016/0112631 A1 | 4/2016 | Ackley et al. |
| 2016/0112643 A1 | 4/2016 | Laffargue et al. |
| 2016/0124516 A1 | 5/2016 | Schoon et al. |
| 2016/0125217 A1 | 5/2016 | Todeschini |
| 2016/0125342 A1 | 5/2016 | Miller et al. |
| 2016/0132707 A1 | 5/2016 | Lindbo et al. |
| 2016/0133253 A1 | 5/2016 | Braho et al. |
| 2016/0171720 A1 | 6/2016 | Todeschini |
| 2016/0178479 A1 | 6/2016 | Goldsmith |
| 2016/0180678 A1 | 6/2016 | Ackley et al. |
| 2016/0188944 A1 | 6/2016 | Wilz et al. |
| 2016/0189087 A1 | 6/2016 | Morton et al. |
| 2016/0125873 A1 | 7/2016 | Braho et al. |
| 2016/0227912 A1 | 8/2016 | Oberpriller et al. |
| 2016/0232891 A1 | 8/2016 | Pecorari |
| 2016/0292477 A1 | 10/2016 | Bidwell |
| 2016/0294779 A1 | 10/2016 | Yeakley et al. |
| 2016/0306769 A1 | 10/2016 | Kohtz et al. |
| 2016/0314276 A1 | 10/2016 | Sewell et al. |
| 2016/0314294 A1 | 10/2016 | Kubler et al. |

FOREIGN PATENT DOCUMENTS

| | | |
|---|---|---|
| WO | 2014019130 A1 | 2/2014 |
| WO | 2014110495 A1 | 7/2014 |

OTHER PUBLICATIONS

Kapoor et al., "Combining brain computer interfaces with vision for object categorization", Computer Vision and Pattern Recognition, IEEE Conference on 2008, accessible online at http://ieeexplore.ieee.org/document/4587618/, pp. 1-8 [Cited in GB Search Report].

Behroozi et al., "EEG phase patterns reflect the representation of semantic categories of objects", B. Med. Biol. Eng. Comput. (2016) 54:205, Sep. 23, 2015, accessible online at http://rd.springer.com/article/10.1007%2Fs11517-015-1391-7, pp. 1-28 [Cited in GB Search Report].

U.S. Appl. No. 13/367,978, filed Feb. 7, 2012, (Feng et al.); now abandoned.

U.S. Appl. No. 14/277,337 for Multipurpose Optical Reader, filed May 14, 2014 (Jovanovski et al.); 59 pages; now abandoned.

U.S. Appl. No. 14/446,391 for Multifunction Point of Sale Apparatus With Optical Signature Capture filed Jul. 30, 2014 (Good et al.); 37 pages; now abandoned.

U.S. Appl. No. 29/516,892 for Table Computer filed Feb. 6, 2015 (Bidwell et al.); 13 pages.

U.S. Appl. No. 29/523,098 for Handle for a Tablet Computer filed Apr. 7, 2015 (Bidwell et al.); 17 pages.

U.S. Appl. No. 29/528,890 for Mobile Computer Housing filed Jun. 2, 2015 (Fitch et al.); 61 pages.

U.S. Appl. No. 29/526,918 for Charging Base filed May 14, 2015 (Fitch et al.); 10 pages.

U.S. Appl. No. 14/715,916 for Evaluating Image Values filed May 19, 2015 (Ackley); 60 pages.

U.S. Appl. No. 29/525,068 for Tablet Computer With Removable Scanning Device filed Apr. 27, 2015 (Schulte et al.); 19 pages.

U.S. Appl. No. 29/468,118 for an Electronic Device Case, filed Sep. 26, 2013 (Oberpriller et al.); 44 pages.

U.S. Appl. No. 29/530,600 for Cyclone filed Jun. 18, 2015 (Vargo et al); 16 pages.

U.S. Appl. No. 14/707,123 for Application Independent DEX/UCS Interface filed May 8, 2015 (Pape); 47 pages.

U.S. Appl. No. No. 14/283,282 for Terminal Having Illumination and Focus Control filed May 21, 2014 (Liu et al.); 31 pages; now abandoned.

U.S. Appl. No. 14/705,407 for Method and System to Protect Software-Based Network-Connected Devices From Advanced Persistent Threat filed May 6, 2015 (Hussey et al.); 42 pages.

U.S. Appl. No. 14/704,050 for Intermediate Linear Positioning filed May 5, 2015 (Charpentier et al.); 60 pages.

U.S. Appl. No. 14/705,012 for Hands-Free Human Machine Interface Responsive to a Driver of a Vehicle filed May 6, 2015 (Fitch et al.); 44 pages.

U.S. Appl. No. 14/715,672 for Augumented Reality Enabled Hazard Display filed May 19, 2015 (Venkatesha et al.); 35 pages.

U.S. Appl. No. 14/735,717 for Indicia-Reading Systems Having an Interface With a User's Nervous System filed Jun. 10, 2015 (Todeschini); 39 pages.

U.S. Appl. No. 14/702,110 for System and Method for Regulating Barcode Data Injection Into a Running Application on a Smart Device filed May 1, 2015 (Todeschini et al.); 38 pages.

U.S. Appl. No. 14/747,197 for Optical Pattern Projector filed Jun. 23, 2015 (Thuries et al.); 33 pages.

U.S. Appl. No. 14/702,979 for Tracking Battery Conditions filed May 4, 2015 (Young et al.); 70 pages.

U.S. Appl. No. 29/529,441 for Indicia Reading Device filed Jun. 8, 2015 (Zhou et al.); 14 pages.

U.S. Appl. No. 14/747,490 for Dual-Projector Three-Dimensional Scanner filed Jun. 23, 2015 (Jovanovski et al.); 40 pages.

U.S. Appl. No. 14/740,320 for Tactile Switch for a Mobile Electronic Device filed Jun. 16, 2015 (Barndringa); 38 pages.

U.S. Appl. No. 14/740,373 for Calibrating a Volume Dimensioner filed Jun. 16, 2015 (Ackley et al.); 63 pages.

Wikipedia, "Evoked potential" downloaded from: https://en.wikipedia.org/wiki/Evoked_potential, Sep. 17, 2015, pp. 1-9.

Combined Search and Examination Report in related GB Application No. 1721791.0, dated Feb. 19, 2018, pp. 1-9 [All references previously cited.].

\* cited by examiner

PRODUCT IDENTIFICATION USING ELECTROENCEPHALOGRAPHY

FIELD OF THE INVENTION

The present invention relates to product identification, as for example in point of sale terminals using Electroencephalography (EEG).

BACKGROUND

Generally speaking, barcode scanning, in particular two dimensional barcode scanning, requires a great deal of image processing, the image to be in perfect focus and adequate lighting conditions. Accurate scanning can be hindered when these conditions are not met or when there is excessive motion. In addition, the barcode should ideally be properly positioned within the field of view of an imager, which may be unintuitive to aim. If any of these preconditions are not met, the barcode often cannot be deciphered. Also, sometimes the barcode itself is printed poorly and can be damaged during the life of the product. This can lead to hard or impossible to read codes. Some items, such as produce, often do not even have barcodes and have to be keyed in manually by a cashier. This can be time consuming and can be impeded by human error. It is also quite simple for a thief to swap the barcode of an expensive item with the barcode of a much cheaper product. These issues can cause major problems and be very expensive for businesses.

Therefore, a need exists for a system that enhances bar code reading or replaces the bar code reading with another system.

SUMMARY

Accordingly, in one aspect, the present invention embraces use of EEG data to aid in identification of items in order to process a Point-Of-Sale transaction.

In an example embodiment, an EEG POS system has an EEG device that detects electrical signals representing brain waves. A database of brain wave profiles represents a plurality of items to be identified. A live signal analyzer compares electrical signals from the EEG device with stored brain wave profiles in the database to identify entries in the database representing items that match the electrical signals from the EEG device, where items whose stored brain wave profiles match the electrical signals are considered identified items. A POS terminal is coupled to the live signal analyzer in order to log and tally items for a transaction.

In another example embodiment, an electroencephalograph (EEG) point of sale system having an EEG device that is configured to detect a plurality of electrical signals representing brain waves. A database of brain wave profiles represent a plurality of items to be identified. A live signal analyzer compares electrical signals from the EEG device with stored brain wave profiles in the database to identify entries in the database representing items that match the electrical signals from the EEG device, where items whose stored brain wave profiles match the electrical signals are considered identified items.

In certain example implementations, the system also has a point of sale terminal coupled to the live signal analyzer that logs and tallies items for a transaction, where the live signal analyzer provides item identification and price data to the point of sale terminal for identified items. In certain example implementations, the live signal analyzer comprises a programmed processor coupled to the EEG device, the point of sale terminal, and the database. In certain example implementations, the EEG device is configured as headgear that is to be worn by a user. In certain example implementations, a brain response profiler generates a brain response profile for an item from the EEG device and generates a database entry for the item.

In certain example implementations, the brain response profiler is implemented using a programmed processor coupled to the EEG device and the database. In certain example implementations, the live signal analyzer identifies entries in the database representing items that match the electrical signals from the EEG device by cross correlating the plurality of electrical signals from the EEG device with stored database entries representing a plurality of items. In certain example implementations, the electrical signals from the EEG device are converted to frequency domain signals and where the brain response profile is a frequency domain profile.

In yet another example embodiment, 9. A method, involves receiving electroencephalograph (EEG) data generated when a user is exposed to an item that is to be identified; at a programmed processor, comparing the EEG data to a plurality of brain wave profiles stored in a database, the stored brain wave profiles corresponding to identifiable items; ascertaining that a match exists between the EEG data and a stored brain wave profile for a particular identifiable item; retrieving information from the database associated with the particular identifiable item; and passing the information retrieved from the database to a point of sale terminal.

In certain example implementations, the information retrieved from the database comprises item identification and price data. In certain example implementations, the comparing comprises calculating a cross correlation between the EEG data and a plurality of the stored brain wave profiles. In certain example implementations, the method further involves processing the EEG data using a fast Fourier transform. In certain example implementations, the EEG data and the brain wave profiles are represented in the frequency domain.

In another aspect, the present invention involves a training method, including receiving EEG training data from an EEG device that is generated when a user is exposed to a training item; generating an item brain wave profile for the training item that characterizes the EEG training data along with data identifying the training item; and storing the item brain wave profile in a database.

In certain example implementations, the method further involves receiving electroencephalograph (EEG) data generated when a user is exposed to an item that is to be identified; at a programmed processor, comparing the EEG data to a plurality of item brain wave profiles stored in the database; ascertaining that a match exists between the EEG data and a stored item brain wave profile for a particular identifiable item; retrieving information from the database associated with the particular identifiable item; and passing the information retrieved from the database to a point of sale terminal.

In certain example implementations, the information retrieved from the database includes item identification and price data. In certain example implementations, the comparing involves calculating a cross correlation between the EEG data and a plurality of the stored brain wave profiles. In certain example implementations, processing the EEG data involves using a fast Fourier transform. In certain example implementations, the EEG data and the brain wave profiles are represented in the frequency domain.

The foregoing illustrative summary, as well as other exemplary objectives and/or advantages of the invention, and the manner in which the same are accomplished, are further explained within the following detailed description and its accompanying drawings.

DETAILED DESCRIPTION

Figure 1:
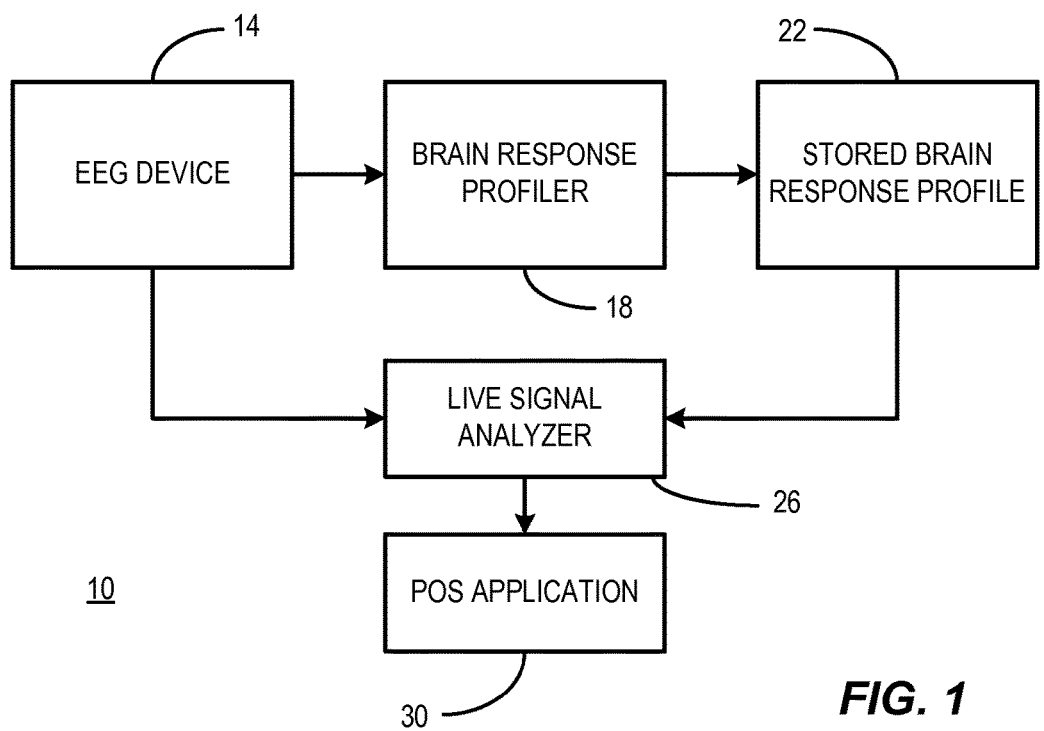
FIG. 1 depicts a logical block diagram of a system consistent with certain example embodiments consistent with the present invention.

The present invention embraces methods and apparatus using electroencephalograph data to scan items to be checked out at a point of sale terminal, for example, at a retail establishment.

As previously noted barcode scanning, in particular two dimensional barcode scanning, requires a great deal of image processing, minimal motion, perfect focus, proper placement in a scanner's field, clear bar code printing and adequate lighting conditions. Accurate scanning can be hindered when these conditions are not met. If any of these preconditions are not met, the barcode often cannot be deciphered.

As the form factor of our products continue to evolve, so too will the way in which we interact with them. Today there are several ways of interfacing with smart devices other than traditional hardware buttons. Touch screen gesturing, voice recognition, inertial sensors motion detection, 3D sensor gesture recognition and other methods have become commonplace for interfacing with a computer. More recently, many advances have been made in improvements in the brain-computer interface (BCI). All BCI devices on the market today use electroencephalography (EEG) as their core technology. This involves the placement of an array of electrodes on the head, which measure voltage fluctuations resulting from ionic current flows within the neurons of the brain. These electromagnetic signals are recorded, processed and the source of the activity is isolated.

Embodiments consistent with the present invention can address the above problems by removing most of the preconditions necessary to successfully identify a product. It removes the need for any image processing, any mechanical autofocus routine, can operate in extremely low light conditions, and is motion tolerant. It also removes the need for a barcode altogether, thus eliminating all the issues regarding print quality, code damage, and theft. It also facilitates the identification of items like produce, which typically do not contain barcodes. This is done by replacing or supplementing the current method of product identification using a barcode scanner with the human brain in cooperation with EEG technology.

Recent advances in Electroencephalography (EEG) have taken the ability to read electronic signals produced by the brain out of the lab and into to more mainstream applications. Relatively inexpensive EEG devices have been brought to market that do not require shaving of the subject's head or gels of any kind. Such devices can be easily worn by the user and are quite unobtrusive and even stylish.

In accord with the present discussion, an EEG device is used to identify a product that is being viewed without the use of barcode technology and unreliable image processing (or as a supplement thereto). Certain embodiments utilize the extremely efficient object recognition algorithms ingrained within the human brain to determine what object is currently being looked at. Such embodiments also capitalize on the focusing and light sensitivity powers of the human eye to make sure the object is always in focus and perfectly exposed. Real-time readings from the EEG may be compared to known readings that have been previously cataloged for the current user. In other words, certain embodiments of this invention aim to heavily leverage what hundreds of thousands of years of evolution have given humans.

In accord with certain embodiments, an Electroencephalography (EEG) device, e.g. such as devices similar to the Emotiv EPOC product (Commercially available from Emotiv, Inc., 490 Post St. Suite 824, San Francisco, Calif. 94102 USA) is used to characterize brain waves for purposes of identifying products at checkout. In one example, a training process is conducted in which a retail store clerk is shown all or a portion of the products available for sale in a store while wearing the EEG device. The employee's brain response to the sight of each object can be recorded and cataloged for that particular employee. After training is complete there will exist a catalog of unique brain responses (for each employee) paired with an identifier for each product within the system.

In the example of a grocery store, when products are placed on a checkout conveyor belt, the store clerk wearing the EEG device simply needs to look at each item individually while bagging them. The EEG device produces an EEG representation of the clerk's brain responses. This EEG representation is then compared to the pre-cataloged list of responses acquired during employee training to identify the products that are currently being looked at. When matches are obtained between the current EEG signal and the pre-cataloged list of responses are found, visual and/or audible feedback can be produced for the clerk in order to confirm to the clerk that the product has been identified. The system can record the associated item and its price for checkout.

This technology can be used standalone or combined with existing bar code reader technology, or can be paired with eye direction detection, so that one barcode in a field can be selected and trigger the scan of the desired code.

An exemplary embodiment is depicted from a logical block diagram perspective as system 10 of FIG. 1 in which an EEG device 14 produces signals that represent brain waves of a user when viewing an object. While training this device to the brain wave signals of a particular user, a brain response profiler 18 receives signals from each of a plurality (e.g., sixteen) of electrodes affixed to the user's scalp. This placement of the electrodes can be accomplished using headgear equipped with EEG electrodes as the EEG device 14.

The brain wave signals represented by voltages picked up at each of the electrodes is processed by the brain response profiler to generate a profile for the user's brain waves when the user is presented with a visual (and possibly tactile) exposure to an item that is to be profiled. Such a profile is generated for each of a plurality of items representing inventory in a retail establishment. The profile of the brain waves is associated with an identifier of the item and a price to be charged for that item to complete a profile record for each of the items to be processed. The profile can then be stored to a database to produce stored brain response profiles 22.

When the brain response profiles 22 are completed for each item, the training process is complete. The brain wave signals during normal operation of a user (e.g., a retail clerk) from EEG device 14 are then passed to a live signal analyzer 26. The live signal analyzer 26 receives the EEG signals as the user views items that are to be checked out one at a time. The live signal analyzer 26 generates a profile in a manner similar to the brain response profiler 18 and conducts a comparison of the live brain response profile with the stored brain response profiles stored at 22 in order to identify a close match. This can be accomplished using any number of techniques including cross-correlation of the profiles to seek the highest correlation. When a match is achieved, the item is identified by the live signal analyzer and the identity of the item and price is transferred to a point of sale (POS) application for tallying and logging for use in completing the retail transaction.

Figure 2:
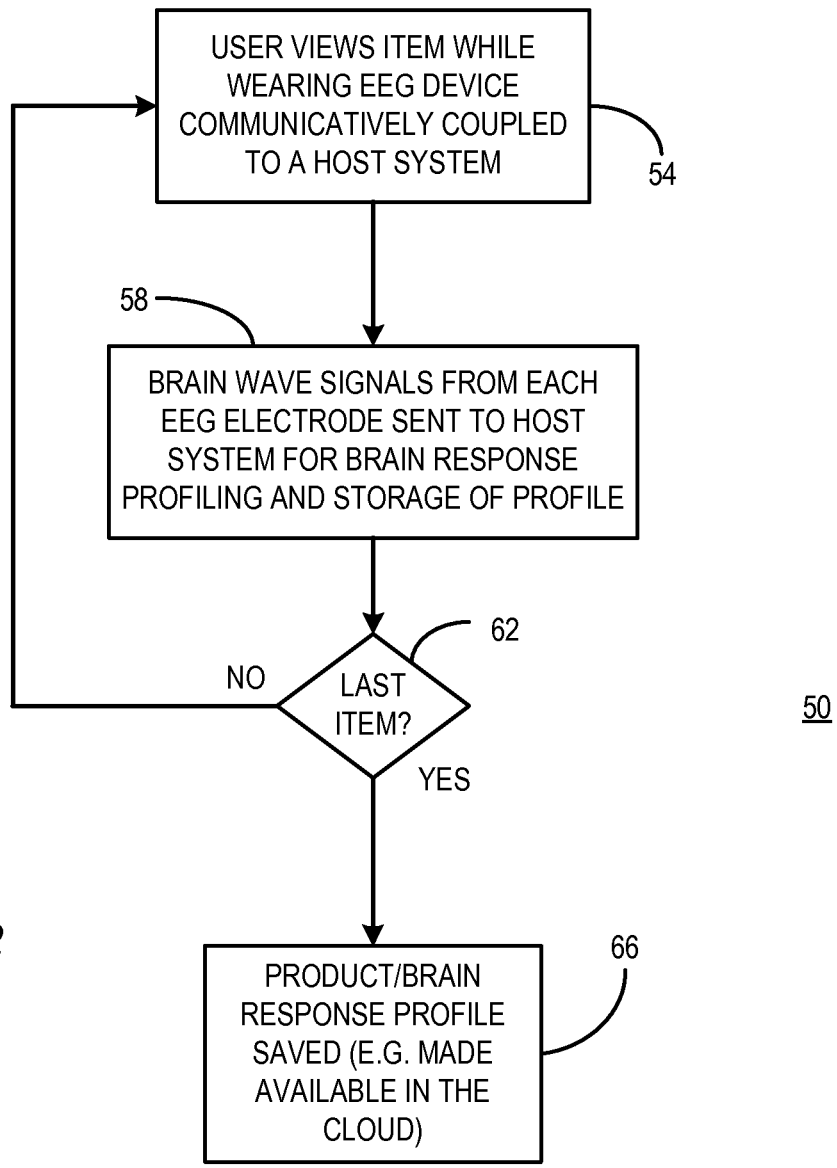
FIG. 2 is an example of a flow chart depicting a training process as used with certain example embodiments consistent with the present invention.

Referring now to FIG. 2, a training process is described in connection with example block diagram 50 starting at 54 where the user being trained views items while wearing an EEG device that is communicatively coupled to a host computer system. As an item is being viewed, the brain wave signals associated with the item is sent from each of the EEG electrodes to the host system for brain response profiling and storage of the brain response profile at 58. If the last item to be trained has not been reached at 62, the user then proceeds to the next item at 54 and the process is repeated. When the last item has been reached at 62, the profile of each product and the brain response profile associated therewith can be stored (e.g., to cloud storage) for later retrieval during the operational process.

Figure 3:
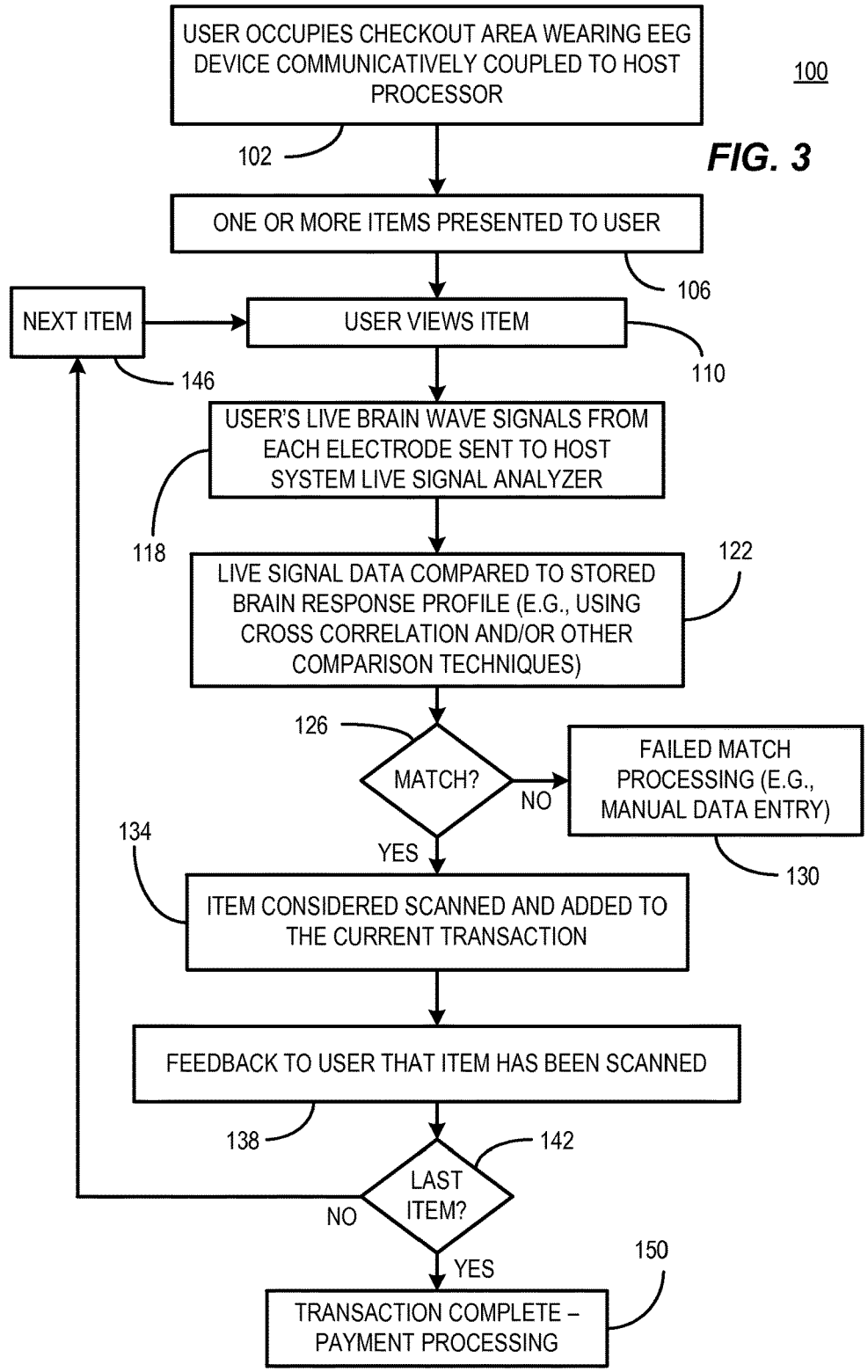
FIG. 3 is an example of a flow chart depicting an operational process as used in certain example embodiments consistent with the present invention.

Referring now to FIG. 3, an operational process for use of the EEG technology for item identification in a retail environment by a user such as a store clerk is depicted in example flow chart 100 starting at 102. At 102, a user occupies the checkout area wearing an EEG device that is wired or wirelessly coupled to a host processor. A transaction is initiated and the user is presented with one or more items for checkout in a normal manner at 106. One by one, the user views each item at 110 to produce a brain wave response that is represented by the signals from each of the electrodes of the EEG device and sent to a host system's live signal analyzer at 118.

The host system's live signal analyzer compares the live EEG signals with stored brain response profiles for the user at 122 in order to identify a matching item in the brain response/product profiles. If no match is achieved at 126, a failure routine is entered at 130 to allow for other data entry techniques. Moreover, excessive failures to identify an item may be indicative of an improperly installed EEG device or a need for further training to better characterize the items that are to be identified.

When a match is achieved at 126, the item is considered "scanned" and identified at 134 and it can be logged to the current transaction along with an identifier of the item and a price to be charged. Feedback can be generated at 138 upon completion of a scan to let the user know that the item has been successfully scanned and the next item (if any) can be viewed. If the item is not the last item at 142, the next item is retrieved at 146 and control passes to 110 to repeat the process. When the last item is reached at 142, the transaction can enter a final stage in which payment is processed at 150 and the transaction can be deemed completed.

Figure 4:
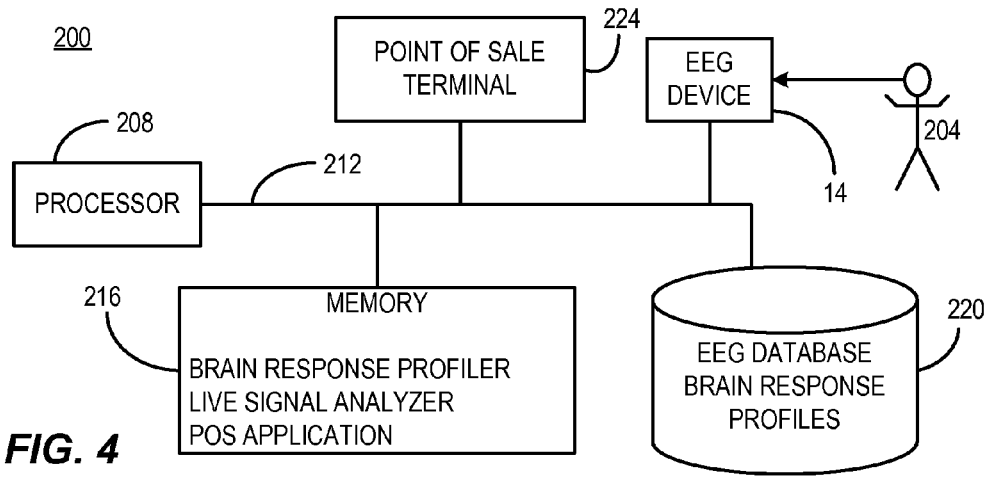
FIG. 4 is an example system block diagram for an illustrative system consistent with the present teachings.

Turning now to FIG. 4, an example system 200 is depicted. A user 204 is connected to an EEG device 14 that is suitably interfaced to a host processor 208 either with a wired connection such as a universal serial bus (USB) connection or via a wireless connection. The connection of EEG device 14 is represented functionally in this illustration as a connection to bus 212 of the system 200.

The host processor 208 may be locally or remotely situated or cloud based without limitation. Moreover, processor 208 can be made up of one processor or a plurality of processors. The processor 208 is coupled to memory 216 that includes routines or modules that correspond to the functions of brain response profiler, live signal analyzer, and Point-Of-Sale applications. Processor is further communicatively coupled to EEG database 220 that contains entries corresponding to brain wave profiles and other data for a plurality of identifiable items. Processor 208 is further communicatively coupled to a Point-Of-Sale terminal 224 that is used to carry out a financial transaction with a customer.

During the training process discussed above, the EEG device 14 measures brain wave signals from the user as the user views and/or is otherwise exposed to an item that could be purchased. The brain response profiler operation is carried out by processor 208 to create a profile of each item and the profile is then stored in the database 220.

During live operation, the user 204 is exposed to items that are being purchased and the associated live EEG data is produced by EEG device 14. This live EEG data is analyzed by the processor 208 using the live signal analyzer process to conduct a comparison between the live EEG data and the EEG database entries to identify the item. Once the item is identified, information such as an item name or description can be retrieved from the database along with price for the item. This information is then transferred to the POS application for use at the POS terminal to complete a transaction by adding the item to a list of items being purchased and adding the price to a transaction tally.

Figure 5:
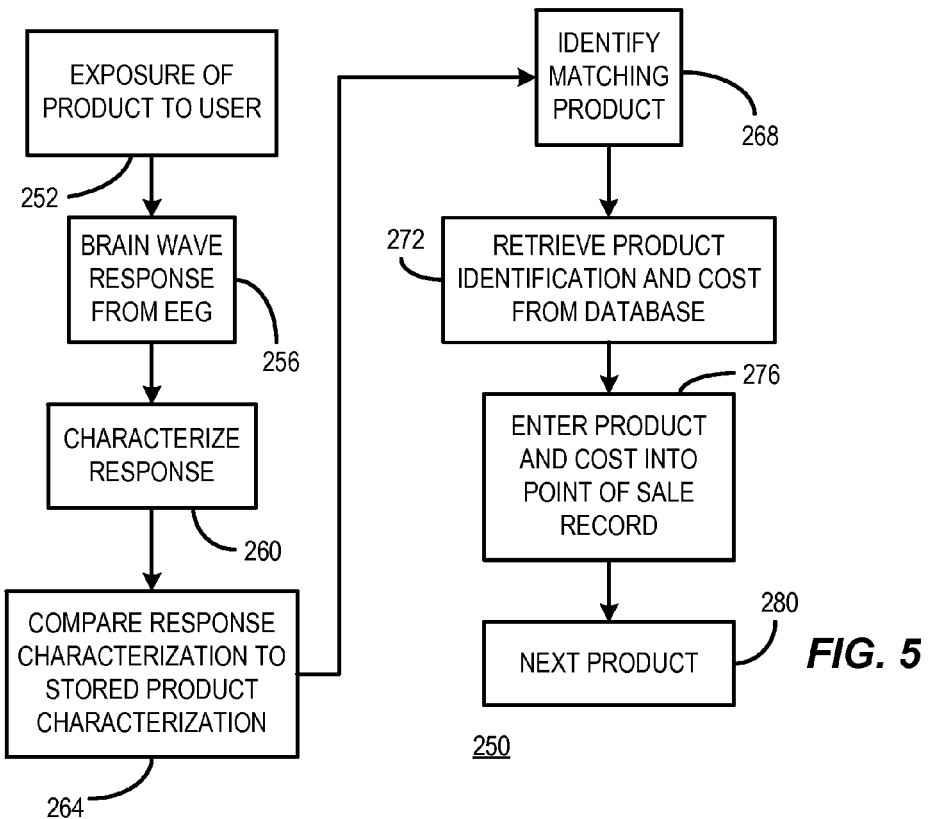
FIG. 5 is an example of a flow chart of an overall process including training and operation of an example system consistent with the present invention.

An example of the operation of system while carrying out a live transaction is depicted in one example by the flow chart 250 of FIG. 5 start starting at 252 where the user is exposed to a product to be identified. Electroencephalograph (EEG) data is generated when the user is exposed to an item that is to be identified at 256. The raw data from the EEG can be used or the EEG data can be converted to a characterization of the EEG response at 260. The processor then compares the EEG data to a plurality of brain wave profiles stored in a database at 264, where the stored brain wave profiles corresponding to identifiable items in the database. At 268, the process ascertains that a match exists between the EEG data and a stored brain wave profile for a particular identifiable item. Information is retrieved from the database entry associated with the particular identifiable item at 272 (e.g., an identification of the item and a cost). The retrieved information can then be transferred at 276 from the database to the point of sale terminal so that the price and item identifier can be entered into the POS transaction record. The system is then ready to process the next product at 280.

EEG technology is used to measure brain activity which is generally classified by frequency bands: Delta ($\delta$, below 4 Hz), Theta ($\theta$, 4-7 Hz), Alpha ($\alpha$, 8-12 Hz), Beta ($\beta$, 13-30 Hz) and Gamma ($\gamma$, above 30 Hz). The output of an EEG device is a collection of signals picked up by sensors placed about a user's head, which picks up brain activity, in the form of measured voltage fluctuations resulting from ionic current within the neurons of the brain, in the above frequency bands. These signals can represent intensity and frequency of brain waves as received by each of the sensors. In accord with the present teachings, a collection of such signals received by a plurality of sensors can be used as a "signature" that identifies a user's brain activity when visually stimulated by viewing a particular object.

An evoked potential is the electrical response of the brain to a stimulus. In the present case, the EEG device measures electrical potentials at the electrodes that are evoked in response to visual stimulation of the brain when the user is exposed to an item that is to be identified. In general, N sensors (e.g., N=16) in an EEG device will produce N output signals which may, in certain implementations, be represented as a sequence of K samples of the electrical potential present at each of the electrodes. So, for N electrodes, one form of EEG output can be represented as a matrix as shown:

| Sample 1 | V1(1) | V2(1) | V3(1) | V4(1) ... VN(1) |
| Sample 2 | V1(2) | V2(2) | V3(2) | V4(2) ... VN(2) |
| ... | | | | |
| Sample K | V1(K) | V2(K) | V3(K) | V4(K) ... VN(K) |

In one embodiment consistent with the present teachings, this matrix of sample values (or a normalized version thereof) can be used directly as a brain wave profile for storage in the database along with other information such as the following simple record for an example item:

| Item Name | Price | Per | Profile |
|---|---|---|---|
| Watermelon | $6.95 | Each | [watermelon profile matrix] |

It will be appreciated that when items are sold by weight, after recognizing the item, the actual cost that is tallied for checkout will factor in the weight of the product. It is further noted that the above example profile is somewhat minimalist since the database can also store other data such as inventory related data, manufacturer or supplier, rebate information and other data.

During operation, the live EEG data as read by the EEG device can be arranged in a matrix in the same manner as that used in the profile and then compared to the profile matrices stored in the database using any suitable comparison technique to identify an item in the database that can be considered a match for the item represented by the Live EEG data.

Many variations are possible. For example, the profile data for a particular item (as well as the live EEG data representation) can be processed to either simplify calculations or enhance accuracy. In one example, data averaging techniques can be used. In other examples, the time domain sample data can be processed by a fast Fourier transform (FFT) to convert the data to a sequence of samples representing the brain waves in the frequency domain. In yet other examples, the frequency domain data can be added together and possibly normalized in order to construct a composite set of data for the set of N electrodes. This may reduce the volume of data and allow for classification of the data to facilitate enhancement of speed of carrying out the comparison operations.

Those skilled in the art will appreciate that other techniques for manipulation and interpretation of EEG signals can be utilized including those which involve averaging the EEG activity time-locked to the presentation of a stimulus and other techniques known in the field of signal processing and EEG interpretation for cognitive science, cognitive psychology, and psychophysiology. Algorithms to determine what is considered a match and what type of tolerance is acceptable can be determined experimentally.

* * *

To supplement the present disclosure, this application incorporates entirely by reference the following commonly assigned patents, patent application publications, and patent applications:

U.S. Pat. Nos. 6,832,725; 7,128,266; 7,159,783; 7,413,127; 7,726,575; 8,294,969; 8,317,105; 8,322,622; 8,366,005; 8,371,507; 8,376,233; 8,381,979; 8,390,909; 8,408,464; 8,408,468; 8,408,469; 8,424,768; 8,448,863; 8,457,013; 8,459,557; 8,469,272; 8,474,712; 8,479,992; 8,490,877; 8,517,271; 8,523,076; 8,528,818; 8,544,737; 8,548,242; 8,548,420; 8,550,335; 8,550,354; 8,550,357; 8,556,174; 8,556,176; 8,556,177; 8,559,767; 8,599,957; 8,561,895; 8,561,903; 8,561,905; 8,565,107; 8,571,307; 8,579,200; 8,583,924; 8,584,945; 8,587,595; 8,587,697; 8,588,869; 8,590,789; 8,596,539; 8,596,542; 8,596,543; 8,599,271; 8,599,957; 8,600,158; 8,600,167; 8,602,309; 8,608,053; 8,608,071; 8,611,309; 8,615,487; 8,616,454; 8,621,123; 8,622,303; 8,628,013; 8,628,015; 8,628,016; 8,629,926; 8,630,491; 8,635,309; 8,636,200; 8,636,212; 8,636,215; 8,636,224; 8,638,806; 8,640,958; 8,640,960; 8,643,717; 8,646,692; 8,646,694; 8,657,200; 8,659,397; 8,668,149; 8,678,285; 8,678,286; 8,682,077; 8,687,282; 8,692,927; 8,695,880; 8,698,949; 8,717,494; 8,717,494; 8,720,783; 8,723,804; 8,723,904; 8,727,223; D702,237; 8,740,082; 8,740,085; 8,746,563; 8,750,445; 8,752,766; 8,756,059; 8,757,495; 8,760,563; 8,763,909; 8,777,108; 8,777,109; 8,779,898; 8,781,520; 8,783,573; 8,789,757; 8,789,758; 8,789,759; 8,794,520; 8,794,522; 8,794,525; 8,794,526; 8,798,367; 8,807,431; 8,807,432; 8,820,630; 8,822,848; 8,824,692; 8,824,696; 8,842,849; 8,844,822; 8,844,823; 8,849,019; 8,851,383; 8,854,633; 8,866,963; 8,868,421; 8,868,519; 8,868,802; 8,868,803; 8,870,074; 8,879,639; 8,880,426; 8,881,983; 8,881,987; 8,903,172; 8,908,995; 8,910,870; 8,910,875; 8,914,290; 8,914,788; 8,915,439; 8,915,444; 8,916,789; 8,918,250; 8,918,564; 8,925,818; 8,939,374; 8,942,480; 8,944,313; 8,944,327; 8,944,332; 8,950,678; 8,967,468; 8,971,346; 8,976,030; 8,976,368; 8,978,981; 8,978,983; 8,978,984; 8,985,456; 8,985,457; 8,985,459; 8,985,461; 8,988,578; 8,988,590; 8,991,704; 8,996,194; 8,996,384; 9,002,641; 9,007,368; 9,010,641; 9,015,513; 9,016,576; 9,022,288; 9,030,964; 9,033,240; 9,033,242; 9,036,054; 9,037,344; 9,038,911; 9,038,915; 9,047,098; 9,047,359; 9,047,420; 9,047,525; 9,047,531; 9,053,055; 9,053,378; 9,053,380; 9,058,526; 9,064,165; 9,064,167; 9,064,168; 9,064,254; 9,066,032; 9,070,032;

U.S. Design Pat. Nos. D716,285; D723,560; D730,357; D730,901; D730,902; D733,112; D734,339;

International Publication No. 2013/163789; International Publication No. 2013/173985; International Publication No. 2014/019130; International Publication No. 2014/110495;

U.S. Patent Application Publication No. 2008/0185432; U.S. Patent Application Publication No. 2009/0134221; U.S. Patent Application Publication No. 2010/0177080; U.S. Patent Application Publication No. 2010/0177076; U.S. Patent Application Publication No. 2010/0177707; U.S. Patent Application Publication No. 2010/0177749; U.S.

Patent Application Publication No. 2010/0265880; U.S.
Patent Application Publication No. 2011/0202554; U.S.
Patent Application Publication No. 2012/0111946; U.S.
Patent Application Publication No. 2012/0168511; U.S.
Patent Application Publication No. 2012/0168512; U.S.
Patent Application Publication No. 2012/0193423; U.S.
Patent Application Publication No. 2012/0203647; U.S.
Patent Application Publication No. 2012/0223141; U.S.
Patent Application Publication No. 2012/0228382; U.S.
Patent Application Publication No. 2012/0248188; U.S.
Patent Application Publication No. 2013/0043312; U.S.
Patent Application Publication No. 2013/0082104; U.S.
Patent Application Publication No. 2013/0175341; U.S.
Patent Application Publication No. 2013/0175343; U.S.
Patent Application Publication No. 2013/0257744; U.S.
Patent Application Publication No. 2013/0257759; U.S.
Patent Application Publication No. 2013/0270346; U.S.
Patent Application Publication No. 2013/0287258; U.S.
Patent Application Publication No. 2013/0292475; U.S.
Patent Application Publication No. 2013/0292477; U.S.
Patent Application Publication No. 2013/0293539; U.S.
Patent Application Publication No. 2013/0293540; U.S.
Patent Application Publication No. 2013/0306728; U.S.
Patent Application Publication No. 2013/0306731; U.S.
Patent Application Publication No. 2013/0307964; U.S.
Patent Application Publication No. 2013/0308625; U.S.
Patent Application Publication No. 2013/0313324; U.S.
Patent Application Publication No. 2013/0313325; U.S.
Patent Application Publication No. 2013/0342717; U.S.
Patent Application Publication No. 2014/0001267; U.S.
Patent Application Publication No. 2014/0008439; U.S.
Patent Application Publication No. 2014/0025584; U.S.
Patent Application Publication No. 2014/0034734; U.S.
Patent Application Publication No. 2014/0036848; U.S.
Patent Application Publication No. 2014/0039693; U.S.
Patent Application Publication No. 2014/0042814; U.S.
Patent Application Publication No. 2014/0049120; U.S.
Patent Application Publication No. 2014/0049635; U.S.
Patent Application Publication No. 2014/0061306; U.S.
Patent Application Publication No. 2014/0063289; U.S.
Patent Application Publication No. 2014/0066136; U.S.
Patent Application Publication No. 2014/0067692; U.S.
Patent Application Publication No. 2014/0070005; U.S.
Patent Application Publication No. 2014/0071840; U.S.
Patent Application Publication No. 2014/0074746; U.S.
Patent Application Publication No. 2014/0076974; U.S.
Patent Application Publication No. 2014/0078341; U.S.
Patent Application Publication No. 2014/0078345; U.S.
Patent Application Publication No. 2014/0097249; U.S.
Patent Application Publication No. 2014/0098792; U.S.
Patent Application Publication No. 2014/0100813; U.S.
Patent Application Publication No. 2014/0103115; U.S.
Patent Application Publication No. 2014/0104413; U.S.
Patent Application Publication No. 2014/0104414; U.S.
Patent Application Publication No. 2014/0104416; U.S.
Patent Application Publication No. 2014/0104451; U.S.
Patent Application Publication No. 2014/0106594; U.S.
Patent Application Publication No. 2014/0106725; U.S.
Patent Application Publication No. 2014/0108010; U.S.
Patent Application Publication No. 2014/0108402; U.S.
Patent Application Publication No. 2014/0110485; U.S.
Patent Application Publication No. 2014/0114530; U.S.
Patent Application Publication No. 2014/0124577; U.S.
Patent Application Publication No. 2014/0124579; U.S.
Patent Application Publication No. 2014/0125842; U.S.
Patent Application Publication No. 2014/0125853; U.S.
Patent Application Publication No. 2014/0125999; U.S.
Patent Application Publication No. 2014/0129378; U.S.
Patent Application Publication No. 2014/0131438; U.S.
Patent Application Publication No. 2014/0131441; U.S.
Patent Application Publication No. 2014/0131443; U.S.
Patent Application Publication No. 2014/0131444; U.S.
Patent Application Publication No. 2014/0131445; U.S.
Patent Application Publication No. 2014/0131448; U.S.
Patent Application Publication No. 2014/0133379; U.S.
Patent Application Publication No. 2014/0136208; U.S.
Patent Application Publication No. 2014/0140585; U.S.
Patent Application Publication No. 2014/0151453; U.S.
Patent Application Publication No. 2014/0152882; U.S.
Patent Application Publication No. 2014/0158770; U.S.
Patent Application Publication No. 2014/0159869; U.S.
Patent Application Publication No. 2014/0166755; U.S.
Patent Application Publication No. 2014/0166759; U.S.
Patent Application Publication No. 2014/0168787; U.S.
Patent Application Publication No. 2014/0175165; U.S.
Patent Application Publication No. 2014/0175172; U.S.
Patent Application Publication No. 2014/0191644; U.S.
Patent Application Publication No. 2014/0191913; U.S.
Patent Application Publication No. 2014/0197238; U.S.
Patent Application Publication No. 2014/0197239; U.S.
Patent Application Publication No. 2014/0197304; U.S.
Patent Application Publication No. 2014/0214631; U.S.
Patent Application Publication No. 2014/0217166; U.S.
Patent Application Publication No. 2014/0217180; U.S.
Patent Application Publication No. 2014/0231500; U.S.
Patent Application Publication No. 2014/0232930; U.S.
Patent Application Publication No. 2014/0247315; U.S.
Patent Application Publication No. 2014/0263493; U.S.
Patent Application Publication No. 2014/0263645; U.S.
Patent Application Publication No. 2014/0267609; U.S.
Patent Application Publication No. 2014/0270196; U.S.
Patent Application Publication No. 2014/0270229; U.S.
Patent Application Publication No. 2014/0278387; U.S.
Patent Application Publication No. 2014/0278391; U.S.
Patent Application Publication No. 2014/0282210; U.S.
Patent Application Publication No. 2014/0284384; U.S.
Patent Application Publication No. 2014/0288933; U.S.
Patent Application Publication No. 2014/0297058; U.S.
Patent Application Publication No. 2014/0299665; U.S.
Patent Application Publication No. 2014/0312121; U.S.
Patent Application Publication No. 2014/0319220; U.S.
Patent Application Publication No. 2014/0319221; U.S.
Patent Application Publication No. 2014/0326787; U.S.
Patent Application Publication No. 2014/0332590; U.S.
Patent Application Publication No. 2014/0344943; U.S.
Patent Application Publication No. 2014/0346233; U.S.
Patent Application Publication No. 2014/0351317; U.S.
Patent Application Publication No. 2014/0353373; U.S.
Patent Application Publication No. 2014/0361073; U.S.
Patent Application Publication No. 2014/0361082; U.S.
Patent Application Publication No. 2014/0362184; U.S.
Patent Application Publication No. 2014/0363015; U.S.
Patent Application Publication No. 2014/0369511; U.S.
Patent Application Publication No. 2014/0374483; U.S.
Patent Application Publication No. 2014/0374485; U.S.
Patent Application Publication No. 2015/0001301; U.S.
Patent Application Publication No. 2015/0001304; U.S.
Patent Application Publication No. 2015/0003673; U.S.
Patent Application Publication No. 2015/0009338; U.S.
Patent Application Publication No. 2015/0009610; U.S.
Patent Application Publication No. 2015/0014416; U.S.
Patent Application Publication No. 2015/0021397; U.S.
Patent Application Publication No. 2015/0028102; U.S.
Patent Application Publication No. 2015/0028103; U.S.

Patent Application Publication No. 2015/0028104; U.S. Patent Application Publication No. 2015/0029002; U.S. Patent Application Publication No. 2015/0032709; U.S. Patent Application Publication No. 2015/0039309; U.S. Patent Application Publication No. 2015/0039878; U.S. Patent Application Publication No. 2015/0040378; U.S. Patent Application Publication No. 2015/0048168; U.S. Patent Application Publication No. 2015/0049347; U.S. Patent Application Publication No. 2015/0051992; U.S. Patent Application Publication No. 2015/0053766; U.S. Patent Application Publication No. 2015/0053768; U.S. Patent Application Publication No. 2015/0053769; U.S. Patent Application Publication No. 2015/0060544; U.S. Patent Application Publication No. 2015/0062366; U.S. Patent Application Publication No. 2015/0063215; U.S. Patent Application Publication No. 2015/0063676; U.S. Patent Application Publication No. 2015/0069130; U.S. Patent Application Publication No. 2015/0071819; U.S. Patent Application Publication No. 2015/0083800; U.S. Patent Application Publication No. 2015/0086114; U.S. Patent Application Publication No. 2015/0088522; U.S. Patent Application Publication No. 2015/0096872; U.S. Patent Application Publication No. 2015/0099557; U.S. Patent Application Publication No. 2015/0100196; U.S. Patent Application Publication No. 2015/0102109; U.S. Patent Application Publication No. 2015/0115035; U.S. Patent Application Publication No. 2015/0127791; U.S. Patent Application Publication No. 2015/0128116; U.S. Patent Application Publication No. 2015/0129659; U.S. Patent Application Publication No. 2015/0133047; U.S. Patent Application Publication No. 2015/0134470; U.S. Patent Application Publication No. 2015/0136851; U.S. Patent Application Publication No. 2015/0136854; U.S. Patent Application Publication No. 2015/0142492; U.S. Patent Application Publication No. 2015/0144692; U.S. Patent Application Publication No. 2015/0144698; U.S. Patent Application Publication No. 2015/0144701; U.S. Patent Application Publication No. 2015/0149946; U.S. Patent Application Publication No. 2015/0161429; U.S. Patent Application Publication No. 2015/0169925; U.S. Patent Application Publication No. 2015/0169929; U.S. Patent Application Publication No. 2015/0178523; U.S. Patent Application Publication No. 2015/0178534; U.S. Patent Application Publication No. 2015/0178535; U.S. Patent Application Publication No. 2015/0178536; U.S. Patent Application Publication No. 2015/0178537; U.S. Patent Application Publication No. 2015/0181093; U.S. Patent Application Publication No. 2015/0181109;

U.S. patent application Ser. No. 13/367,978 for a Laser Scanning Module Employing an Elastomeric U-Hinge Based Laser Scanning Assembly, filed Feb. 7, 2012 (Feng et al.);

U.S. patent application Ser. No. 29/458,405 for an Electronic Device, filed Jun. 19, 2013 (Fitch et al.);

U.S. patent application Ser. No. 29/459,620 for an Electronic Device Enclosure, filed Jul. 2, 2013 (London et al.);

U.S. patent application Ser. No. 29/468,118 for an Electronic Device Case, filed Sep. 26, 2013 (Oberpriller et al.);

U.S. patent application Ser. No. 14/150,393 for Indicia-reader Having Unitary Construction Scanner, filed Jan. 8, 2014 (Colavito et al.);

U.S. patent application Ser. No. 14/200,405 for Indicia Reader for Size-Limited Applications filed Mar. 7, 2014 (Feng et al.);

U.S. patent application Ser. No. 14/231,898 for Hand-Mounted Indicia-Reading Device with Finger Motion Triggering filed Apr. 1, 2014 (Van Horn et al.);

U.S. patent application Ser. No. 29/486,759 for an Imaging Terminal, filed Apr. 2, 2014 (Oberpriller et al.);

U.S. patent application Ser. No. 14/257,364 for Docking System and Method Using Near Field Communication filed Apr. 21, 2014 (Showering);

U.S. patent application Ser. No. 14/264,173 for Autofocus Lens System for Indicia Readers filed Apr. 29, 2014 (Ackley et al.);

U.S. patent application Ser. No. 14/277,337 for MULTIPURPOSE OPTICAL READER, filed May 14, 2014 (Jovanovski et al.);

U.S. patent application Ser. No. 14/283,282 for TERMINAL HAVING ILLUMINATION AND FOCUS CONTROL filed May 21, 2014 (Liu et al.);

U.S. patent application Ser. No. 14/327,827 for a MOBILE-PHONE ADAPTER FOR ELECTRONIC TRANSACTIONS, filed Jul. 10, 2014 (Hejl);

U.S. patent application Ser. No. 14/334,934 for a SYSTEM AND METHOD FOR INDICIA VERIFICATION, filed Jul. 18, 2014 (Hejl);

U.S. patent application Ser. No. 14/339,708 for LASER SCANNING CODE SYMBOL READING SYSTEM, filed Jul. 24, 2014 (Xian et al.);

U.S. patent application Ser. No. 14/340,627 for an AXIALLY REINFORCED FLEXIBLE SCAN ELEMENT, filed Jul. 25, 2014 (Rueblinger et al.);

U.S. patent application Ser. No. 14/446,391 for MULTIFUNCTION POINT OF SALE APPARATUS WITH OPTICAL SIGNATURE CAPTURE filed Jul. 30, 2014 (Good et al.);

U.S. patent application Ser. No. 14/452,697 for INTERACTIVE INDICIA READER, filed Aug. 6, 2014 (Todeschini);

U.S. patent application Ser. No. 14/453,019 for DIMENSIONING SYSTEM WITH GUIDED ALIGNMENT, filed Aug. 6, 2014 (Li et al.);

U.S. patent application Ser. No. 14/462,801 for MOBILE COMPUTING DEVICE WITH DATA COGNITION SOFTWARE, filed on Aug. 19, 2014 (Todeschini et al.);

U.S. patent application Ser. No. 14/483,056 for VARIABLE DEPTH OF FIELD BARCODE SCANNER filed Sep. 10, 2014 (McCloskey et al.);

U.S. patent application Ser. No. 14/513,808 for IDENTIFYING INVENTORY ITEMS IN A STORAGE FACILITY filed Oct. 14, 2014 (Singel et al.);

U.S. patent application Ser. No. 14/519,195 for HANDHELD DIMENSIONING SYSTEM WITH FEEDBACK filed Oct. 21, 2014 (Laffargue et al.);

U.S. patent application Ser. No. 14/519,179 for DIMENSIONING SYSTEM WITH MULTIPATH INTERFERENCE MITIGATION filed Oct. 21, 2014 (Thuries et al.);

U.S. patent application Ser. No. 14/519,211 for SYSTEM AND METHOD FOR DIMENSIONING filed Oct. 21, 2014 (Ackley et al.);

U.S. patent application Ser. No. 14/519,233 for HANDHELD DIMENSIONER WITH DATA-QUALITY INDICATION filed Oct. 21, 2014 (Laffargue et al.);

U.S. patent application Ser. No. 14/519,249 for HANDHELD DIMENSIONING SYSTEM WITH MEASUREMENT-CONFORMANCE FEEDBACK filed Oct. 21, 2014 (Ackley et al.);

U.S. patent application Ser. No. 14/527,191 for METHOD AND SYSTEM FOR RECOGNIZING SPEECH USING WILDCARDS IN AN EXPECTED RESPONSE filed Oct. 29, 2014 (Braho et al.);

U.S. patent application Ser. No. 14/529,563 for ADAPTABLE INTERFACE FOR A MOBILE COMPUTING DEVICE filed Oct. 31, 2014 (Schoon et al.);

U.S. patent application Ser. No. 14/529,857 for BARCODE READER WITH SECURITY FEATURES filed Oct. 31, 2014 (Todeschini et al.);

U.S. patent application Ser. No. 14/398,542 for PORTABLE ELECTRONIC DEVICES HAVING A SEPARATE LOCATION TRIGGER UNIT FOR USE IN CONTROLLING AN APPLICATION UNIT filed Nov. 3, 2014 (Bian et al.);

U.S. patent application Ser. No. 14/531,154 for DIRECTING AN INSPECTOR THROUGH AN INSPECTION filed Nov. 3, 2014 (Miller et al.);

U.S. patent application Ser. No. 14/533,319 for BARCODE SCANNING SYSTEM USING WEARABLE DEVICE WITH EMBEDDED CAMERA filed Nov. 5, 2014 (Todeschini);

U.S. patent application Ser. No. 14/535,764 for CONCATENATED EXPECTED RESPONSES FOR SPEECH RECOGNITION filed Nov. 7, 2014 (Braho et al.);

U.S. patent application Ser. No. 14/568,305 for AUTO-CONTRAST VIEWFINDER FOR AN INDICIA READER filed Dec. 12, 2014 (Todeschini);

U.S. patent application Ser. No. 14/573,022 for DYNAMIC DIAGNOSTIC INDICATOR GENERATION filed Dec. 17, 2014 (Goldsmith);

U.S. patent application Ser. No. 14/578,627 for SAFETY SYSTEM AND METHOD filed Dec. 22, 2014 (Ackley et al.);

U.S. patent application Ser. No. 14/580,262 for MEDIA GATE FOR THERMAL TRANSFER PRINTERS filed Dec. 23, 2014 (Bowles);

U.S. patent application Ser. No. 14/590,024 for SHELVING AND PACKAGE LOCATING SYSTEMS FOR DELIVERY VEHICLES filed Jan. 6, 2015 (Payne);

U.S. patent application Ser. No. 14/596,757 for SYSTEM AND METHOD FOR DETECTING BARCODE PRINTING ERRORS filed Jan. 14, 2015 (Ackley);

U.S. patent application Ser. No. 14/416,147 for OPTICAL READING APPARATUS HAVING VARIABLE SETTINGS filed Jan. 21, 2015 (Chen et al.);

U.S. patent application Ser. No. 14/614,706 for DEVICE FOR SUPPORTING AN ELECTRONIC TOOL ON A USER'S HAND filed Feb. 5, 2015 (Oberpriller et al.);

U.S. patent application Ser. No. 14/614,796 for CARGO APPORTIONMENT TECHNIQUES filed Feb. 5, 2015 (Morton et al.);

U.S. patent application Ser. No. 29/516,892 for TABLE COMPUTER filed Feb. 6, 2015 (Bidwell et al.);

U.S. patent application Ser. No. 14/619,093 for METHODS FOR TRAINING A SPEECH RECOGNITION SYSTEM filed Feb. 11, 2015 (Pecorari);

U.S. patent application Ser. No. 14/628,708 for DEVICE, SYSTEM, AND METHOD FOR DETERMINING THE STATUS OF CHECKOUT LANES filed Feb. 23, 2015 (Todeschini);

U.S. patent application Ser. No. 14/630,841 for TERMINAL INCLUDING IMAGING ASSEMBLY filed Feb. 25, 2015 (Gomez et al.);

U.S. patent application Ser. No. 14/635,346 for SYSTEM AND METHOD FOR RELIABLE STORE-AND-FORWARD DATA HANDLING BY ENCODED INFORMATION READING TERMINALS filed Mar. 2, 2015 (Sevier);

U.S. patent application Ser. No. 29/519,017 for SCANNER filed Mar. 2, 2015 (Zhou et al.);

U.S. patent application Ser. No. 14/405,278 for DESIGN PATTERN FOR SECURE STORE filed Mar. 9, 2015 (Zhu et al.);

U.S. patent application Ser. No. 14/660,970 for DECODABLE INDICIA READING TERMINAL WITH COMBINED ILLUMINATION filed Mar. 18, 2015 (Kearney et al.);

U.S. patent application Ser. No. 14/661,013 for REPROGRAMMING SYSTEM AND METHOD FOR DEVICES INCLUDING PROGRAMMING SYMBOL filed Mar. 18, 2015 (Soule et al.);

U.S. patent application Ser. No. 14/662,922 for MULTIFUNCTION POINT OF SALE SYSTEM filed Mar. 19, 2015 (Van Horn et al.);

U.S. patent application Ser. No. 14/663,638 for VEHICLE MOUNT COMPUTER WITH CONFIGURABLE IGNITION SWITCH BEHAVIOR filed Mar. 20, 2015 (Davis et al.);

U.S. patent application Ser. No. 14/664,063 for METHOD AND APPLICATION FOR SCANNING A BARCODE WITH A SMART DEVICE WHILE CONTINUOUSLY RUNNING AND DISPLAYING AN APPLICATION ON THE SMART DEVICE DISPLAY filed Mar. 20, 2015 (Todeschini);

U.S. patent application Ser. No. 14/669,280 for TRANSFORMING COMPONENTS OF A WEB PAGE TO VOICE PROMPTS filed Mar. 26, 2015 (Funyak et al.);

U.S. patent application Ser. No. 14/674,329 for AIMER FOR BARCODE SCANNING filed Mar. 31, 2015 (Bidwell);

U.S. patent application Ser. No. 14/676,109 for INDICIA READER filed Apr. 1, 2015 (Huck);

U.S. patent application Ser. No. 14/676,327 for DEVICE MANAGEMENT PROXY FOR SECURE DEVICES filed Apr. 1, 2015 (Yeakley et al.);

U.S. patent application Ser. No. 14/676,898 for NAVIGATION SYSTEM CONFIGURED TO INTEGRATE MOTION SENSING DEVICE INPUTS filed Apr. 2, 2015 (Showering);

U.S. patent application Ser. No. 14/679,275 for DIMENSIONING SYSTEM CALIBRATION SYSTEMS AND METHODS filed Apr. 6, 2015 (Laffargue et al.);

U.S. patent application Ser. No. 29/523,098 for HANDLE FOR A TABLET COMPUTER filed Apr. 7, 2015 (Bidwell et al.);

U.S. patent application Ser. No. 14/682,615 for SYSTEM AND METHOD FOR POWER MANAGEMENT OF MOBILE DEVICES filed Apr. 9, 2015 (Murawski et al.);

U.S. patent application Ser. No. 14/686,822 for MULTIPLE PLATFORM SUPPORT SYSTEM AND METHOD filed Apr. 15, 2015 (Qu et al.);

U.S. patent application Ser. No. 14/687,289 for SYSTEM FOR COMMUNICATION VIA A PERIPHERAL HUB filed Apr. 15, 2015 (Kohtz et al.);

U.S. patent application Ser. No. 29/524,186 for SCANNER filed Apr. 17, 2015 (Zhou et al.);

U.S. patent application Ser. No. 14/695,364 for MEDICATION MANAGEMENT SYSTEM filed Apr. 24, 2015 (Sewell et al.);

U.S. patent application Ser. No. 14/695,923 for SECURE UNATTENDED NETWORK AUTHENTICATION filed Apr. 24, 2015 (Kubler et al.);

U.S. patent application Ser. No. 29/525,068 for TABLET COMPUTER WITH REMOVABLE SCANNING DEVICE filed Apr. 27, 2015 (Schulte et al.);

U.S. patent application Ser. No. 14/699,436 for SYMBOL READING SYSTEM HAVING PREDICTIVE DIAGNOSTICS filed Apr. 29, 2015 (Nahill et al.);

U.S. patent application Ser. No. 14/702,110 for SYSTEM AND METHOD FOR REGULATING BARCODE DATA INJECTION INTO A RUNNING APPLICATION ON A SMART DEVICE filed May 1, 2015 (Todeschini et al.);

U.S. patent application Ser. No. 14/702,979 for TRACKING BATTERY CONDITIONS filed May 4, 2015 (Young et al.);

U.S. patent application Ser. No. 14/704,050 for INTERMEDIATE LINEAR POSITIONING filed May 5, 2015 (Charpentier et al.);

U.S. patent application Ser. No. 14/705,012 for HANDS-FREE HUMAN MACHINE INTERFACE RESPONSIVE TO A DRIVER OF A VEHICLE filed May 6, 2015 (Fitch et al.);

U.S. patent application Ser. No. 14/705,407 for METHOD AND SYSTEM TO PROTECT SOFTWARE-BASED NETWORK-CONNECTED DEVICES FROM ADVANCED PERSISTENT THREAT filed May 6, 2015 (Hussey et al.);

U.S. patent application Ser. No. 14/707,037 for SYSTEM AND METHOD FOR DISPLAY OF INFORMATION USING A VEHICLE-MOUNT COMPUTER filed May 8, 2015 (Chamberlin);

U.S. patent application Ser. No. 14/707,123 for APPLICATION INDEPENDENT DEX/UCS INTERFACE filed May 8, 2015 (Pape);

U.S. patent application Ser. No. 14/707,492 for METHOD AND APPARATUS FOR READING OPTICAL INDICIA USING A PLURALITY OF DATA SOURCES filed May 8, 2015 (Smith et al.);

U.S. patent application Ser. No. 14/710,666 for PRE-PAID USAGE SYSTEM FOR ENCODED INFORMATION READING TERMINALS filed May 13, 2015 (Smith);

U.S. patent application Ser. No. 29/526,918 for CHARGING BASE filed May 14, 2015 (Fitch et al.);

U.S. patent application Ser. No. 14/715,672 for AUGMENTED REALITY ENABLED HAZARD DISPLAY filed May 19, 2015 (Venkatesha et al.);

U.S. patent application Ser. No. 14/715,916 for EVALUATING IMAGE VALUES filed May 19, 2015 (Ackley);

U.S. patent application Ser. No. 14/722,608 for INTERACTIVE USER INTERFACE FOR CAPTURING A DOCUMENT IN AN IMAGE SIGNAL filed May 27, 2015 (Showering et al.);

U.S. patent application Ser. No. 29/528,165 for IN-COUNTER BARCODE SCANNER filed May 27, 2015 (Oberpriller et al.);

U.S. patent application Ser. No. 14/724,134 for ELECTRONIC DEVICE WITH WIRELESS PATH SELECTION CAPABILITY filed May 28, 2015 (Wang et al.);

U.S. patent application Ser. No. 14/724,849 for METHOD OF PROGRAMMING THE DEFAULT CABLE INTERFACE SOFTWARE IN AN INDICIA READING DEVICE filed May 29, 2015 (Barten);

U.S. patent application Ser. No. 14/724,908 for IMAGING APPARATUS HAVING IMAGING ASSEMBLY filed May 29, 2015 (Barber et al.);

U.S. patent application Ser. No. 14/725,352 for APPARATUS AND METHODS FOR MONITORING ONE OR MORE PORTABLE DATA TERMINALS (Caballero et al.);

U.S. patent application Ser. No. 29/528,590 for ELECTRONIC DEVICE filed May 29, 2015 (Fitch et al.);

U.S. patent application Ser. No. 29/528,890 for MOBILE COMPUTER HOUSING filed Jun. 2, 2015 (Fitch et al.);

U.S. patent application Ser. No. 14/728,397 for DEVICE MANAGEMENT USING VIRTUAL INTERFACES CROSS-REFERENCE TO RELATED APPLICATIONS filed Jun. 2, 2015 (Caballero);

U.S. patent application Ser. No. 14/732,870 for DATA COLLECTION MODULE AND SYSTEM filed Jun. 8, 2015 (Powilleit);

U.S. patent application Ser. No. 29/529,441 for INDICIA READING DEVICE filed Jun. 8, 2015 (Zhou et al.);

U.S. patent application Ser. No. 14/735,717 for INDICIA-READING SYSTEMS HAVING AN INTERFACE WITH A USER'S NERVOUS SYSTEM filed Jun. 10, 2015 (Todeschini);

U.S. patent application Ser. No. 14/738,038 for METHOD OF AND SYSTEM FOR DETECTING OBJECT WEIGHING INTERFERENCES filed Jun. 12, 2015 (Amundsen et al.);

U.S. patent application Ser. No. 14/740,320 for TACTILE SWITCH FOR A MOBILE ELECTRONIC DEVICE filed Jun. 16, 2015 (Bandringa);

U.S. patent application Ser. No. 14/740,373 for CALIBRATING A VOLUME DIMENSIONER filed Jun. 16, 2015 (Ackley et al.);

U.S. patent application Ser. No. 14/742,818 for INDICIA READING SYSTEM EMPLOYING DIGITAL GAIN CONTROL filed Jun. 18, 2015 (Xian et al.);

U.S. patent application Ser. No. 14/743,257 for WIRELESS MESH POINT PORTABLE DATA TERMINAL filed Jun. 18, 2015 (Wang et al.);

U.S. patent application Ser. No. 29/530,600 for CYCLONE filed Jun. 18, 2015 (Vargo et al);

U.S. patent application Ser. No. 14/744,633 for IMAGING APPARATUS COMPRISING IMAGE SENSOR ARRAY HAVING SHARED GLOBAL SHUTTER CIRCUITRY filed Jun. 19, 2015 (Wang);

U.S. patent application Ser. No. 14/744,836 for CLOUD-BASED SYSTEM FOR READING OF DECODABLE INDICIA filed Jun. 19, 2015 (Todeschini et al.);

U.S. patent application Ser. No. 14/745,006 for SELECTIVE OUTPUT OF DECODED MESSAGE DATA filed Jun. 19, 2015 (Todeschini et al.);

U.S. patent application Ser. No. 14/747,197 for OPTICAL PATTERN PROJECTOR filed Jun. 23, 2015 (Thuries et al.);

U.S. patent application Ser. No. 14/747,490 for DUAL-PROJECTOR THREE-DIMENSIONAL SCANNER filed Jun. 23, 2015 (Jovanovski et al.); and U.S. patent application Ser. No. 14/748,446 for CORDLESS INDICIA READER WITH A MULTIFUNCTION COIL FOR WIRELESS CHARGING AND EAS DEACTIVATION, filed Jun. 24, 2015 (Xie et al.).

* * *

In the specification and/or figures, typical embodiments of the invention have been disclosed. The present invention is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

The invention claimed is:

1. An electroencephalograph (EEG) point of sale system, comprising:
   an EEG device that is configured to detect a plurality of electrical signals representing brain waves;
   a database of brain wave profiles representing a plurality of items to be identified, wherein the brain wave profiles comprise electrical signals corresponding to the brain waves recorded during a training of the EEG point of sale system; and
   a live signal analyzer that compares electrical signals from the EEG device with stored brain wave profiles in the database to identify entries in the database representing items that match the electrical signals from the EEG device, where items whose stored brain wave profiles match the electrical signals are considered identified items.

2. The system according to claim 1, further comprising a point of sale terminal coupled to the live signal analyzer that logs and tallies items for a transaction; and
   where the live signal analyzer provides item identification and price data to the point of sale terminal for identified items.

3. The system according to claim 2, where the live signal analyzer comprises a programmed processor coupled to the EEG device, the point of sale terminal, and the database.

4. The system according to claim 1, where the EEG device is configured as headgear that is to be worn by a user.

5. The system according to claim 1, further comprising a brain response profiler that generates a brain response profile for an item from the EEG device and generates a database entry for the item.

6. The system according to claim 5, where the brain response profiler comprises a programmed processor coupled to the EEG device and the database.

7. The system according to claim 1, where the live signal analyzer identifies entries in the database representing items that match the electrical signals from the EEG device by cross correlating the plurality of electrical signals from the EEG device with stored database entries representing a plurality of items.

8. The system according to claim 1, where the electrical signals from the EEG device are converted to frequency domain signals and where the brain response profile is a frequency domain profile.

9. A method, comprising:
   receiving, at a programmed processor, electroencephalograph (EEG) data generated by an EEG device when a user is exposed to an item that is to be identified;
   comparing, via the programmed processor, the EEG data to a plurality of brain wave profiles stored in a database, the stored brain wave profiles corresponding to identifiable items, wherein the brain wave profiles comprise electrical signals corresponding to the brain waves recorded during a training using the EEG device;
   ascertaining, based upon the results of the comparison, that a match exists between the EEG data and a stored brain wave profile for a particular identifiable item;
   retrieving, via the programmed processor, information from the database associated with the particular identifiable item; and
   passing the information retrieved from the database to a point of sale terminal.

10. The method according to claim 9, where the information retrieved from the database comprises item identification and price data.

11. The method according to claim 9, where the comparing comprises calculating a cross correlation between the EEG data and a plurality of the stored brain wave profiles.

12. The method according to claim 9, further comprising processing the EEG data using a fast Fourier transform.

13. The method according to claim 9, where the EEG data and the brain wave profiles are represented in the frequency domain.

* * * * *